United States Patent [19]
Manian et al.

[11] Patent Number: 5,843,680
[45] Date of Patent: *Dec. 1, 1998

[54] DIFFERENTIAL SEPARATION ASSAY METHODS AND TEST KITS

[75] Inventors: Bala S. Manian, Los Altos Hills; Vartan E. Ghazarossian, Menlo Park; Paul G. Hayter, Los Altos, all of Calif.

[73] Assignee: Biometric Imaging, Inc., Mountain View, Calif.

[*] Notice: The term of this patent shall not extend beyond the expiration date of Pat. No. 5,137,609.

[21] Appl. No.: 425,718

[22] Filed: Apr. 19, 1995

Related U.S. Application Data

[63] Continuation-in-part of Ser. No. 277,161, Jul. 19, 1994, abandoned, which is a continuation of Ser. No. 927,928, Aug. 10, 1992, abandoned, which is a continuation-in-part of Ser. No. 828,407, Jan. 31, 1992, Pat. No. 5,137,609.

[51] Int. Cl.$^6$ ........................ G01N 33/558; G01N 33/573
[52] U.S. Cl. .......................... 435/7.4; 435/7.1; 435/7.92; 435/7.93; 436/501; 436/514; 436/515; 436/516
[58] Field of Search .................................. 435/7.1, 7.92, 435/7.47, 7.93; 436/501, 514, 515, 516

[56] References Cited

U.S. PATENT DOCUMENTS

| | | | |
|---|---|---|---|
| 4,353,982 | 10/1982 | Gomez et al. | 72/130 |
| 4,387,160 | 6/1983 | Gomez et al. | 435/7.4 |
| 4,811,218 | 3/1989 | Hunkapiller et al. | 364/413.01 |
| 4,890,247 | 12/1989 | Sarrine et al. | 364/571.04 |
| 5,055,415 | 10/1991 | Imani et al. | |
| 5,093,235 | 3/1992 | Williams et al. | 435/7.32 |
| 5,096,557 | 3/1992 | Simons | 204/182.8 |
| 5,137,606 | 8/1992 | Manian et al. | 204/180.1 |
| 5,137,609 | 8/1992 | Manian et al. | |
| 5,221,454 | 6/1993 | Manian et al. | 204/299 R |

FOREIGN PATENT DOCUMENTS

WO 91/19983   12/1991   WIPO .

OTHER PUBLICATIONS

Sagawa et al. 1992 Kokaido Igaku Zasshi. 67, 97–80.

Singleton et al. (eds.) 1988. in: Dictionary of Microbiology and Molecular Biology Second Edition. Wiley Interscience Chichester. p. 409.

Neilson et al. 1991 J. Chromatog. 539, 177–185.

Briggs et al. 1990 BioTechniques 9, 598–606.

Sagawa et al. 1992, Hokaido Igaku Zasshi, 67, 67–80.

Singleton et al. (eds.) 1988 in Dictionary of Microbiology and Molectular Biology, Second Edition, Wiley Intesciema Chicoster, p. 409.

Nielson et al. 1991 J. Chromatog. 539, 177–185.

Briggs etal 1990 BioTechniques 9, 598–606.

Van denDool, H. and Kratz, P.D., J. Chromatogr. (1963) 11, 463:471. *A Generalization of the Retention Index System Including Linear Temperature Programmed Gas–Liquid Partition Chromatography.*

Wehrli and Kovats, Helv. Chim.Acta (1959) 42, 2709.

Neilsen, R.G. et al., J. Chromatogr. (1991) 539, 177–185. *Separation of Antibody–Antigen Complexes by Capillary Zone Electrophoresis, Isoelectric Focusing and High–Performance Size–Exclusion Chromatography.*

*Primary Examiner*—Christopher L. Chin

[57] ABSTRACT

Analytes can be detected from among closely related substances by reacting the analyte in a test sample with a labeled binding agent which specifically binds to the analyte to form a complex. The labeled binding agent is supplied in excess, and the complex is identified through a time window relative to the detection of the excess unbound agent. The complex and labeled binding agent are isolated on a separation media and identified by the differential rate of migration.

15 Claims, 10 Drawing Sheets

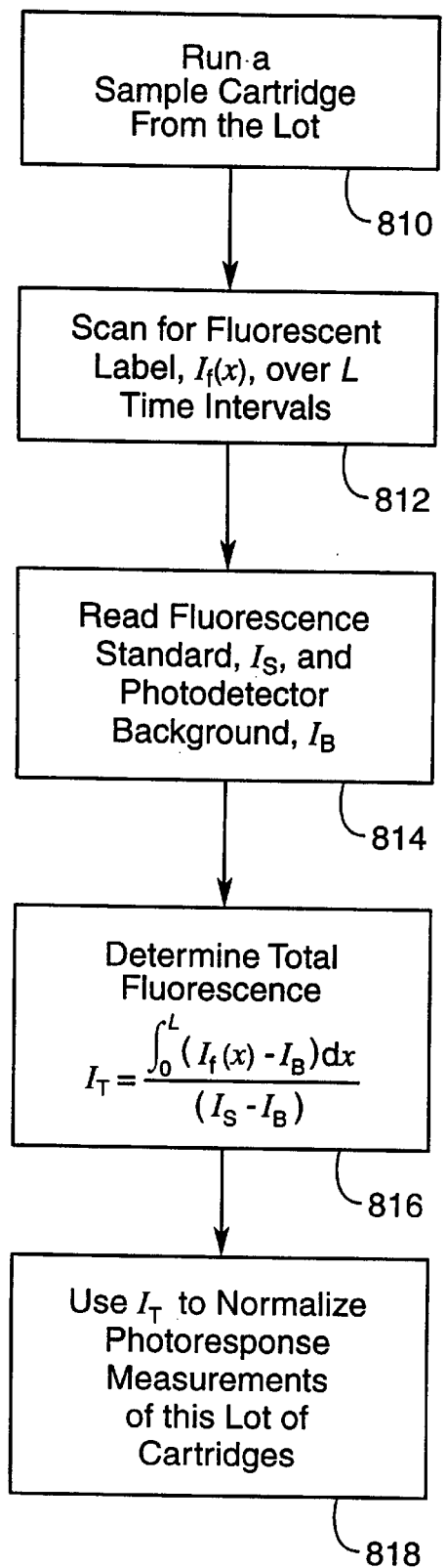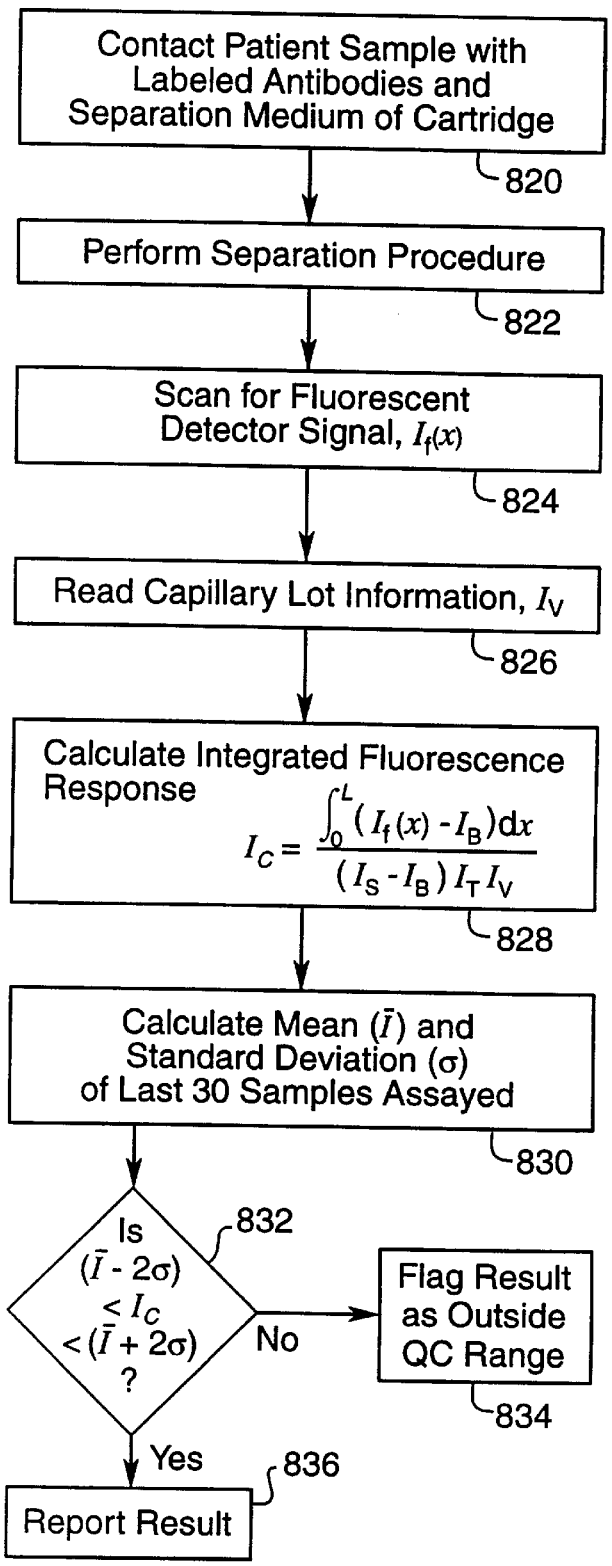
Fig. 12
Fig. 13

DIFFERENTIAL SEPARATION ASSAY METHODS AND TEST KITS

This application is a continuation-in-part division of application Ser. No. 08/277,161 filed Jul. 19, 1994, now abandoned, which is a continuation of application Ser. No. 07/927,928 filed Aug. 10, 1992, now abandoned which is a continuation-in-part of application Ser. No. 07/828,407 filed Jan. 31, 1992, now U.S. Pat. No. 5,137,609.

BACKGROUND OF THE INVENTION

A. Field of the Invention

This invention relates to the field of detecting analytes using agents which specifically bind to the analyte to form complexes, such as antigen/antibody complexes.

B. Description of the Prior Art

There is an extensive body of prior art related analytical techniques based on the formation of complexes between specific binding substances, such as antigens and antibodies; hormones or cell modulators and receptors; avidin/biotin and the like.

*The Journal of Chromatography* 539: 177–185 (1991) and references therein describes the separation of antigen/antibody complexes by capillary zone electrophoresis and isoelectric focusing. In that article, the capillary zone electrophoretic migration of hGH, the antibody to hGH, and the hGH/antibody complex are shown.

*Techniques in Protein Chemistry*, Academic Press, Inc., N.Y., N.Y. (1984), pp. 456–466, describes the purification of antibodies using high performance capillary electrophoresis.

U.S. Pat. No. 4,937,200, Kamazawa, describes the elution of antigens from an antibody packed affinity chromatography column wherein one member of the binding pair is bound to a solid support.

U.S. Pat. No. 5,006,473, Bouma, shows the migration of an alkaline phosphatase labeled antibody in a liposome embedded electrophoresis media. After electrophoresis, the liposome is lysed and a staining dye or reactant is released.

U.S. Pat. Nos. 4,205,058 and 4,301,139 describe a chromatography column which separates antigen and antigen/antibody labeled complexes and the reaction is determined by measuring a radio-labeled antigen which migrates on the column. As an example, T4 $I^{125}$ and anti-T4 are reacted and separated on a cross-linked polyvinyl alcohol column. The antibody/T4 complex is retained at the bottom of the column and the T4 $I^{125}$ migrates. These patents represent an example of the direct binding of a labeled hapten T4 $I^{125}$ and antibody and separation of these complexes.

In U.S. Pat. No. 4,811,218, M. Hunkapiller et al. teach a DNA sequencing system using a multiple lane electrophoresis apparatus. Fluorescent dyes are attached to molecules moving through the lanes. A moving illumination and detection system scans the multiple lanes. Four color data points are recorded for each of several lanes at a particular time at a fixed distance down the gel. Through a complex analytic procedure, the four colors are related to the concentrations of four dye-labeled DNA components. The object is to identify concentrations of A, C, G, or T or G, G+A, C+T or C which are DNA piece endings where A=adenosine, C=cytosine, G=guanine and T=thymine. Peak concentrations of a particular dye label are matched with particular bases in DNA sequences.

In U.S. Pat. No. 4,890,247, Sarrine et al. describe an apparatus which robotically handles a plurality of liquid samples in test tubes, applies the samples to electrophoresis matrices and then carries out electrophoresis. The electrophoretically separated molecules are illuminated with fluorescent light. An analog signal is produced, representing the scanned field of view. A computer stores intensity levels of the analog signal and performs densitometric analysis to read the electrophoretic data. Densitometry is a conventional prior art technique for reading such data.

In an article entitled "Affinity Electrophoresis" by Vaclav Horejsi, reported in *Enzyme Purification and Related Techniques*, W. Jakoby ed., Academic Press, 1984, p. 275, a novel type of electrophoresis is described. One lane of the gel medium is impregnated with immobilized ligands capable of reacting with a migrating macromolecule, while another lane, a control gel, is untreated. Thus, a comparison can be made, using electrophoresis, between a macromolecule sample retarded by the affinity gel lane and a similar sample in the control gel lane. In a variation of this technique, the gel may incorporate an antibody which interacts with a migrating antigen. The two lanes may be calibrated so that different degrees of retardation, for different concentrations of the migrating macromolecule, are known. Moreover, microscopic beads treated with ligands can be entrapped in the gel and similarly serve as a retardant. Beads have the advantage of tight packing in the gel if they are of appropriate size. Activation of the gel involves partial cross-linking so that the gels do not melt on heating. Alternative methods of gel preparation are described, all with the result that a macromolecular retardant is immobilized. Electrophoresis proceeds in the usual way.

Various types of pulsed electrophoresis are known for use in separating closely related substances (see Kreger EPA 457,748; Slater EPA 395,319; Agawa EPA 320,937; and Allington EPA 396,053).

In spite of the above-mentioned advances in analytical separation chemistry, there is still a problem in rapidly separating heavy molecules of close weight or mobility, or charge/mass ratio wherein the analyte and other substances in a test sample exhibit similar behavior in separation efforts. An object of the invention was to devise a method and apparatus for such separations.

SUMMARY OF THE INVENTION

This invention relates to methods and test kits for detecting analytes, in a milieu of substances of closely related weights or mobilities, which specifically bind to a labeled binding reagent to form a complex. The binding agent is labeled with a detectable marker so that binding between the labeled binding agent and analyte provides a reaction mixture which contains a labeled binding agent and a complex of analyte and labeled binding agent. These two labeled substances are placed on a separation medium and the differential rate of migration of the labeled specific binding agent and complex are determined by detecting the label in each as they are being separated on the separation medium. This difference in migration identifies the target analytes. In a preferred embodiment, a second labeled marker is included which migrates different from the labeled binding agent and complex and most preferably migrates faster than the complex or the labeled binding agent.

More specifically, the invention encompasses a method for detecting an analyte in a test sample comprising:

(a) providing a labeled binding agent which specifically binds to the analyte to form a complex;

(b) providing a separation medium on which the labeled binding agent and complex migrate with different velocities; then (c) contacting the test sample with the labeled binding agent to form a complex with analyte in the test sample, both free and bound binding agent having expected migrations from a starting location to one or more measuring places;

(d) separating the labeled binding agent and complex on the separation medium;

(e) measuring and recording the difference in migration between the labeled binding agent and the complex on the separation medium by detecting the labeled binding agent and the labeled binding agent in complex at said measuring places; and (f) searching said recorded migrations for bound binding agent in relation to free binding agent using said expected migrations in comparison to said measured migrations wherein finding of said bound binding agent indicates presence of said analyte.

For example, the analyte may be an antigen and the labeled binding agent a fluorescently labeled antibody or fragment of an antibody such as an Fab fragment.

The labeled binding agent and complex are preferably separated by electrophoresis and the label in each is detected as each migrates passed a fixed point in the electrophoresis medium.

More particularly, the invention also encompasses a method for measuring the concentration of an analyte in a test sample moving in a single lane comprising:

(a) providing a labeled binding agent which specifically binds to the analyte to form a complex;

(b) providing a separation medium on which the labeled binding agent and complex migrate in a single lane with different velocities;

(c) contacting the test sample with an amount of the labeled binding agent in excess of what will react with the analyte to form a complex with analyte in the test sample, both free and bounding binding agent having expected migrations from a starting location to one or more measuring places;

(d) separating the excess labeled binding agent and complex on the separation medium;

(e) measuring and recording the difference in migration between the labeled binding agent and the complex on the separation medium by detecting labeled binding agent and the labeled binding agent in complex at said measuring places;

(f) searching said recorded migrations for bound binding agent in relation to free binding agent using said expected migrations in comparison to said measured migrations wherein finding of said bound binding agent indicates presence of said analyte;

(g) measuring the area under each peak of each characteristic detected label;

(h) normalizing the areas under each peak, and (i) relating the normalized measured areas with the areas of samples containing known amounts of said analyte.

This method can be applied to the measurement of multiple analytes in the same lane or to multiple analytes in different lanes.

A preferred assay utilizes a second labeled marker which migrates independent of the labeled binding agent and complex. Preferably, this second labeled marker migrates first in the medium and serves as a quality control check on the system. For example, if the separation media or other reagent in the test kit are not operative, the failure of the second labeled marker to migrate as expected can be readily detected and the reliability of any results from that assay can be discarded. Also, if the monoclonal antibody or immune complex peak fails to appear in the proper relationship to the second labeled marker, this test may be discarded as faulty.

Another aspect of the invention is test kits which contain an analyte standard, a labeled binding agent which specifically binds to the analyte to form a complex, and a separation medium which separates the labeled binding agent and complex. Such test kits preferably contain a second labeled marker which migrates independent of the labeled binding agent and complex. The separation medium is preferably in the form of a modular cartridge having a plurality of electrophoresis lanes as shown in FIG. 11a. Test kits for detecting an antibody comprise a hapten conjugated labeled carrier, separation medium, and preferably a second labeled marker. A test kit for detecting haptens comprises a hapten conjugated labeled carrier, a standard sample of the hapten, and an antibody to the hapten.

Thus, the present invention takes advantage of the specificity of reaction of specific binding molecules, the ability of separation media to separate small amounts of materials, the sensitivity of detecting labels such as fluorescent labels and a quality control agent to provide rapid, sensitive, and reliable quantitative results. The methods, test kits, and apparatus of this invention are most advantageously applied to closely related and difficult to separate complexes of closely related molecules such as complexes of isoforms of similar proteins. The term "closely related" means not only heavy molecules of close molecular weight, but also molecules whose charge/mass ratio or other characteristic is such that both molecules exhibit similar migration rates, e.g., using electrophoresis, so that previous separation efforts have been difficult. Other features and advantages of the invention will become apparent from the following detailed description, taken in conjunction with the accompanying drawings, which illustrate, by way of example, the features of the invention.

DETAILED DESCRIPTION OF THE INVENTION

The term "analyte" refers to a large variety of chemical substances for which there is a specific binding partner.

It is contemplated that the present assay may be applied to the detection of any analyte for which there is a specific binding partner. The analyte usually is a peptide, protein, carbohydrate, glycoprotein, steroid, or other organic molecule for which a specific binding partner exists in biological systems or can be synthesized. The analyte, in functional terms, is usually selected from the group consisting of antigens and antibodies thereto; haptens and antibodies thereto; and hormones, vitamins, metabolites and pharmacological agents, and their receptors and binding substances. Examples of analytes are immunologically-active polypeptides and proteins of molecular weights between 1,000 and 4,000,000, such as antibodies and antigenic polypeptides and proteins. Other examples of analytes are haptens of molecular weights between 100 and 1,500 which are immunologically active when conjugated to a carrier. Representative of such antigenic polypeptides are angiotensin I and II, C-peptide, oxytocin, vasopressin, neurophysin, gastrin, secretin, and glucagon. Representative of antigenic proteins are insulin, chorionic gonadotropin (e.g., HCG), carcinoembryonic antigen (CEA), myoglobin, hemoglobin, follicle stimulating hormone, human growth hormone, thyroid stimulating hormone (TSH), human placental lactogen, thyroxine binding globulin (TBG), intrinsic factor, transcobalamin, enzymes such as alkaline phosphatase and lactic dehydrogenase, and hepatitis, HTLV-III, influenza, herpes, and other viral associated antigens. Representative of antibody ligands are those antibodies of the IgG, IgE, IgM and IgA classes specific for any of the antigens or haptens, or a class thereof, herein described. The class of hapten ligands is exemplified by thyroxine ($T_4$), triiodothyronine ($T_3$), the estrogens such as estriol, prostaglandins, vitamins such as biotin, vitamin $B_{12}$, folic acid, vitamin E, vitamin A, and ascorbic acid (vitamin C), and drugs such as carbamazepine, quinidine, digoxin, digitoxin, theophylline, phenobarbital, primidone, diphenylhydantoin, morphine, nicotine, and so forth.

DNA, RNA, and their complementary binding sequences and binding proteins can be determined by method of this invention. Cytokines such as interleukins, interferons, G-CSF, GM-CSF, M-CSF, tumor necrosis factors (TNF), erythropoietin and the like are representative of cytokines that may be determined by methods of this invention.

This discussion of analytes is intended to illustrate the large number and variety of chemical substances which have specific binding agents or for which specific binding agents can be made.

The term "labeled binding agent" refers to substances which specifically bind to the analyte and which have a detectable label. The label may be covalently linked or bound to the binding agent indirectly through another specific binding reaction, for example, a labeled goat antihuman antibody could be used to label a human antibody. Those skilled in this art will recognize a wide variety of techniques to label proteinaceous, as well as non-protein specific binding substances. For instance, fluorescent dye labeling of proteins in general and antibodies or antigens in particular is well-known.

For the determination of small analytes, such as those having a molecular weight of 100–1500, it is necessary to prepare a reagent which is a conjugate of the analyte to a labeled carrier. The free analyte in the test sample and analyte on the labeled carrier compete for the specific binding partner prior to separation.

*Current Protocols in Immunology*, edited by John E. Coligan, Ada M. Kruisbeck, David H. Margolies, Ethan M. Shevach, and Warren Strober, John Wiley & Sons, N.Y., 1991, extensively describes methods for obtaining polyclonal and monoclonal antibodies and Fab fragments thereof, means for fluorescently labeling these antibodies and the reactions of these antibodies with antigens. Also described are electrophoresis and electrophoresis media as well as other separation techniques.

A large number of cytokines and monoclonal antibodies to these cytokines are known, for example, interleukin (1 α, 1 β, 2, 3, 4, 5, 6, 7, 8, 9, 10); interferon (α, β, γ); granulocyte/macrophage colony stimulating factor (CN-CSF), G-CSF, M-CSF; tumor necrosis factor (TNFα and β); and Transforming Growth Factor and their monoclonal antibodies are known. Antibodies to creatine kinase (skeletal, cardiac, and brain) are described in U.S. Pat. No. 4,353,982 (Gomez et al.).

Lipopolysaccharide (LPS), an endotoxin, is a major outer membrane component of cell walls of Gram-negative bacteria. Monoclonal antibodies to LPS are well-known, see U.S. Pat. No. 5,092,235 (Williams et al. and references therein).

A specific binding substance may be labeled with any of a variety of dyes, such as fluorescein dyes or rhodamine dyes by conventional chemical techniques. Representative fluorescent dyes for making the labeling binding agent are fluorescein isothiocyanate (emission at 520 nm), 4-chloro-7-nitrobenzo-α-oxa-1-diazole (emission 550 nm), tetramethylrhodamine isothiocyanate (emission 580 nm) Texas Red (emission 610 nm). These dyes are available from Molecular Probes, Inc. (Eugene, Oreg.), or can be synthesized with a variety of functional groups to accommodate the binding of these dyes to various chemical functional groups. For example, fluorescein 5 or 6 succinimidylcarboxylate, fluorescein 5 or 6 iodoacetamide, and fluorescein 5 or 6 maleimide are available. Similar functional groups are available for tetramethylrhodamine dyes.

It is also well-known to indirectly label a specific binding molecular, such as an antibody by specifically binding a second labeled antibody to antibody reagent, such that the detected components are labeled antibody-antibody complex and labeled antibody-antibody-antigen complex.

The term "separation media" refers to size chromatography, affinity and ion exchange chromatography, electrophoresis, such as slab gel electrophoresis or capillary electrophoresis. Media, such as polyacrylamide, cellulose acetate, agar gel, and agarose gel, are suitable for electrophoresis. The separation of the labeled binding agent, complex, and labeled marker can also be achieved by sedimentation techniques where centrifugation causes the component to migrate in the media. These separation techniques are well-known to those skilled in this art.

In its simplest form, the invention involves the reaction of a labeled binding agent (LB*) and an analyte [A] to form a complex A/LB* and separation of these species on a separation media, measuring the differential rate of migration of A/LB* and LB* on the separation media by detecting the label and then using the difference in migration or migration rate to identify the analyte by comparison with calibration data or other data which establishes expected migration data for the analyte.

In another embodiment, multiple analytes can be detected by using different labeled binding agents that specifically bind to each analyte and detecting the LB* and LB*A complex for each label.

In another aspect of this invention, two different labeled binding agents can be bound to one analyte to form a sandwich complex and the migration of the sandwich complex can be compared with either or both of the labeled binding agents.

In yet another embodiment of the present invention, two-dimensional electrophoresis can be used to separate multicomponent systems. In each instance, the differential migration data is compared with expected migration information.

Small molecules such as haptens can be detected by binding the hapten to a labeled carrier [C] such as a polypeptide to form a conjugate in which the hapten or the carrier is labeled (HC*). The hapten in a test sample is allowed to compete with HC* for antihapten and the mixture is separated on the separation media. The species HC* and HC* antibody complex are detected as they separate on the media. This reagent is referred to as a "hapten conjugated labeled carrier."

All of these embodiments are preferably practiced by the inclusion of a second labeled marker which migrates on the separation medium independent of the labeled binding agent and analyte and preferably the second marker is a fluorescent dye derivative which migrates more rapidly than the labeled binding agent and complex in the separation medium. The fluorescent dye can be bound to a protein or other substance which will affect its mobility so that it will migrate as desired in a particular medium. For example, human serum albumin is a negatively charged protein which migrates very rapidly toward the positive pole in electrophoresis. The labeled marker provides for normalization of channel to channel variability in antibody reaction and detection of signal amplitude. It provides an early warning that the particular assay is grossly incorrect. The labeled marker also provides a reference point for discrimination of both the labeled binding agent peak and complex peak, thus further assuring the quality of the assay. The second labeled marker also provides a means for quantitation of the analyte.

This invention is most advantageously applied in the diagnosis of molecular variants of proteins. For example, creatine kinase (CK) MB isoforms (MB2 and MB1) have been used in the early diagnosis of muscle injury following acute myocardial infarction. The determination of the MB2 and MB1 isoforms is also useful in determining the onset of acute cardiac allograft rejection as well as injury following coronary artery bypass grafting. The determination of CKMM isoform is important in monitoring atropic skeletal muscle changes. There is also known to be an increase in mitochondrial creatine kinase in patients with cerebrovascular damages and it is critical that there be a rapid assay to assess such damage so that drug therapy can begin.

The determination of alkaline phosphatase isoforms in liver, bone, and kidney disease, as well as liver transplant rejection. Those skilled in the medical arts will recognize a large number of clinically important proteins which have small differences in structure which can be determined by the method, test kits, and apparatus of this invention.

BRIEF DESCRIPTION OF THE DRAWINGS

FIG. 12 is a flow chart illustrating an embodiment of the assaying technique in accordance with the invention arriving at a normalization factor.

FIG. 13 is a flow chart illustrating an embodiment of the assaying technique in accordance with the invention measuring and normalizing the detected label.

With reference to FIG. 1, a single lane gel electrophoresis apparatus 11 having a well 13 at one end with a negative voltage terminal 16 and a positive high voltage electrode terminal 15 at an opposite end. The electrophoresis apparatus consists of a conventional single lane 18 having a substrate 17, a gel layer 19 and a protective glass cover 21. The substrate is usually a self-supporting material which may be glass, Mylar (Trademark) or any well-known gel support. The gel itself is usually polyacrylamide or agarose, although other gel materials such as synthetic acrylamide substitutes may also be used. Uniform polymerization and freedom from bubbles and irregularities are desirable properties. The glass cover is preferably nonreflective glass which merely serves as a protective cover for the gel. The well 13 is normally positioned vertically so that it will receive a sample without spillage. The well funnels a prepared sample toward the gel. The well may combine a stacking and separating gel and creates a slit of sample material on the gel. High voltage is then applied to the gel at terminals 15, 16 and charged ions migrate toward the positively charged voltage electrode. The end of the gel near well 13 is maintained at negative or ground potential so that there is a substantial potential difference from one end of the gel to the distant end.

Figure 1:
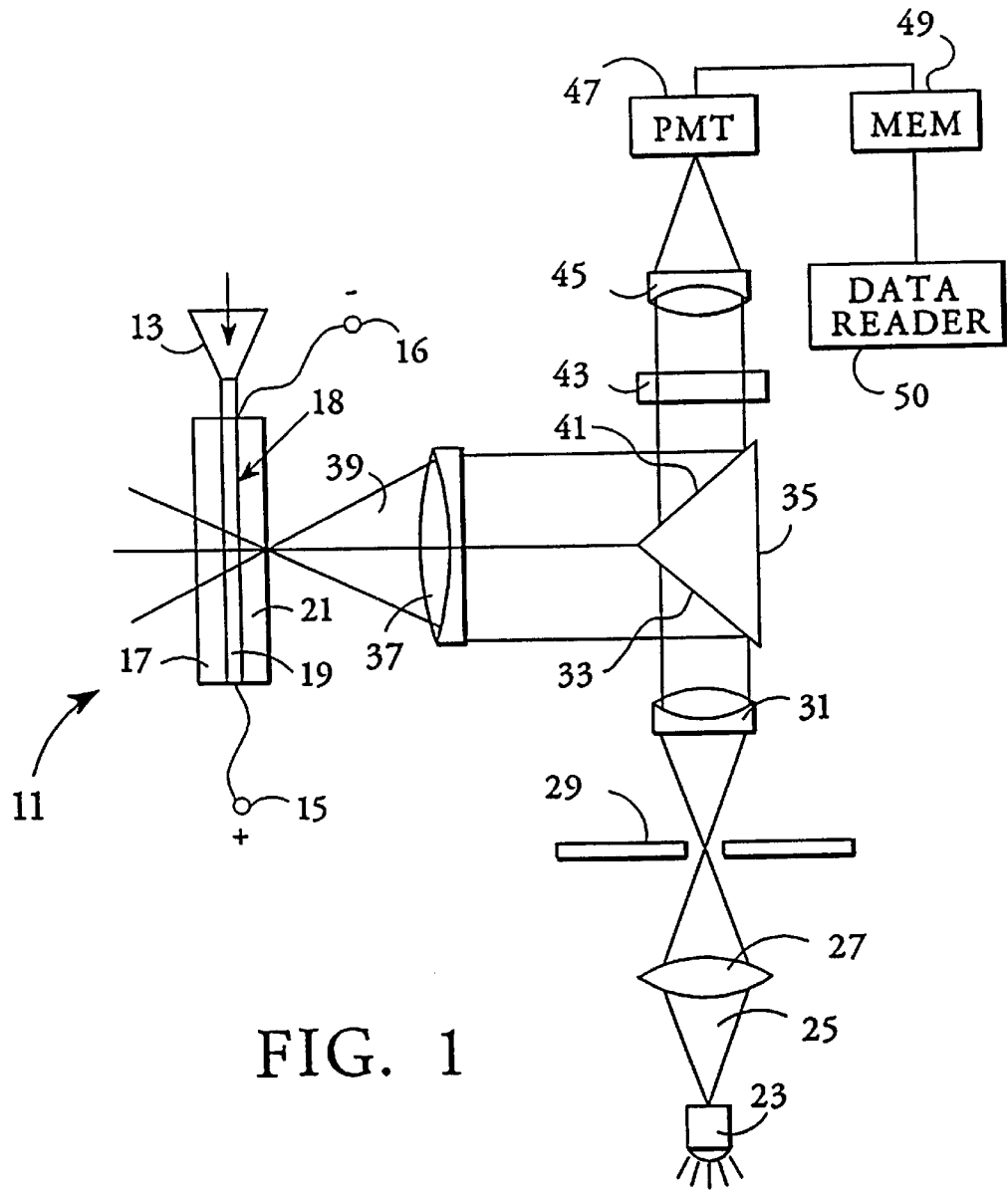
FIG. 1 is a plan view of an apparatus for practicing the present invention.

The sample which is placed in well 13 is a fluid, frequently a fractionated blood sample. Blood may be preprocessed to remove constituents which will interfere with the assay. Removal may be by filtering, absorption, centrifuging or precipitating either the desired or undesired components so that a desired target analyte may be obtained for electrophoresis. The desired target analyte must be one for which there is a specific binding agent. Fluorescent tags such as those commercially available are manufactured by Molecular Probes Inc. of Oregon which specializes in dyes or dyed beads that can be covalently attached to binding agents to provide a labeled binding agent. Where target analytes are found in larger structures, such as pathogenic agents, then such a dye-binding agent conjugate would be appropriate for tracking that pathogenic agent. Monoclonal antibodies can now be manufactured so that the behavior of this binding agent is uniform and predictable for many assays. Monoclonal antibodies are more expensive than polyclonal antibodies, but the antibodies have greater specificity, are directed toward single epitopes, are easy to produce in large quantities and are generally more useful and cause precise separation of bound and free material.

The labeled binding agent is supplied in excess so that the reaction with the analyte will be driven to completion, or nearly to completion in a reasonable or convenient amount of time. The amount of excess labeled binding agent should not be more than twenty times the amount of expected maximum level bound tag, although the number may range between 2 and 50, approximately. The labeling binding agent should alter the mass to charge ratio when combined with the analyte and subjected to an electrophoretic field.

A strongly emitting light source, such as light emitting diode or laser 23 is used to generate a beam 25. The LED 23 has an output power of about 50 mW in a wavelength band which will excite fluorescence in the fluorescent tagging material. Such excitation radiation is known as actinic radiation. The beam is intercepted by a focusing lens 27 which directs the beam through a slit aperture in barrier 29. Light emerging from the slit is divergent and is intercepted by the collimating lens 31. The bean is then directed onto a reflecting surface 33 which is part of a prism 35. The reflective surface 33 is at a 45 degree angle to the beam so that the reflected beam makes a 90 degree angle with the incident beam. The reflected beam is directed toward focusing lens 37 where the beam passes through one half of the focusing lens, while the other half is reserved for light traveling in the opposite direction, reflected from gel layer 19. Light passing through the focusing lens carries an image of the slit 29 which is directed onto the gel layer 19.

Fluorescent light emitted from the complex and some reflected light from the gel layer travels in a retro-beam 39 to the left half of focusing lens 37. Note that one half of the focusing lens is used by light travelling in each direction. The right half is used by the incoming beam, while the left half is used by the retro-beam. From there, the retro-beam is directed to reflecting surface 41 which is part of prism 35. The retro-beam is passed through a filter 43 which rejects any light other than the desired wavelength from the fluorescent target. Light transmitted through the filter is directed toward focusing lens 45. From there the beam is directed to a light detector, such as photomultiplier tube 47 with a slit located at the image plan of the gel.

The time of arrival of the fluorescent substances is measured relative to the starting time, i.e., the application of high voltage which initiates electrophoretic migration. Since the arrival time is not precise, but rather is a Gaussian curve, the peak time is recorded. The integrated peak area is also used for time discrimination. Each analyte and the corresponding labeled binding agent are subject to the same procedure in the calibration run. In calibration runs a mean migration time to the measurement slit or pinhole is determined. Then, the standard deviation is determined for the time of arrival of the free binding agent, as well as for the bound analyte. In the present invention, it is necessary to know the mean migration time, i.e., the expected arrival times of bound and labeled binding agent for analytes because the times will be used to search for target analyte in a sample where the target substance is possibly present, but not necessarily present. The difference in arrival times between the complex and labeled binding agent may be used to establish a time window so that the arrival of one member may be paired with the other member in a search for the other member. If the search reveals that the other member is present within a standard deviation or two, that other material is identified as a member of the pair. If nothing is found within the time window, the first member of the pair is regarded to be an artifact and is discarded. The search may be based on the second labeled marker or any other labeled component.

The output of the photomultiplier tube is maintained in a buffer memory 49 and a ratio may be formed between the signals representing complex and labeled binding agent. A data reader 50 is connected to the buffer memory 49 for receiving recorded signals which represent the fluorescent peaks. The data reader is a computer which correlates the various peaks. Each peak is recorded in order to search for complex and unbound labeled binding agent in the recorded data. Normally, the time of appearance of the labeled binding agent could be estimated from prior calibration times. Once, the position of the free labeled binding agent is known, a search is conducted for the corresponding complex which should be located a certain time interval away, within a search or time window defined by statistical limits. A peak within this window is identified as a complex that will bind fluorescent substance, i.e., the target analyte. Next the amplitudes of the identified peaks are examined and a ratio is computed in the data reader 50. The method whereby labeled binding agent is correlated with complex is explained further below. The computer also stores calibrations of known concentrations of target substance so that ratios may be compared in order to obtain an estimate of the unknown concentration.

Figure 2:
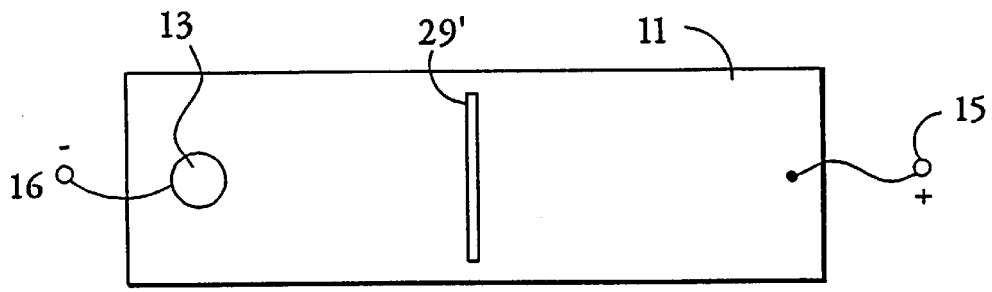
FIG. 2 is a top view of a single gel lane illustrated in FIG. 1.

In FIG. 2, the top view of gel 11 shows that the image 29' of slit 29 falls between a positive high voltage terminal 15 and a slit from well 13, coinciding with negative voltage terminal 16. In operation the high voltage applied to terminal 15 causes migration of complex and labeled binding agents, which are positively or negatively charged molecules which respond to the electric field from the high voltage supply. The labeled binding agent will reach the image 29' of slit 29 which is fixed in position at a time different than the complex. The labeled binding agent serves as one marker for a time window which has the bound tagged binding agent as a corresponding marker, the two markers forming a pair of markers which are separated in time within the statistical limit which is defined.

Figure 3:
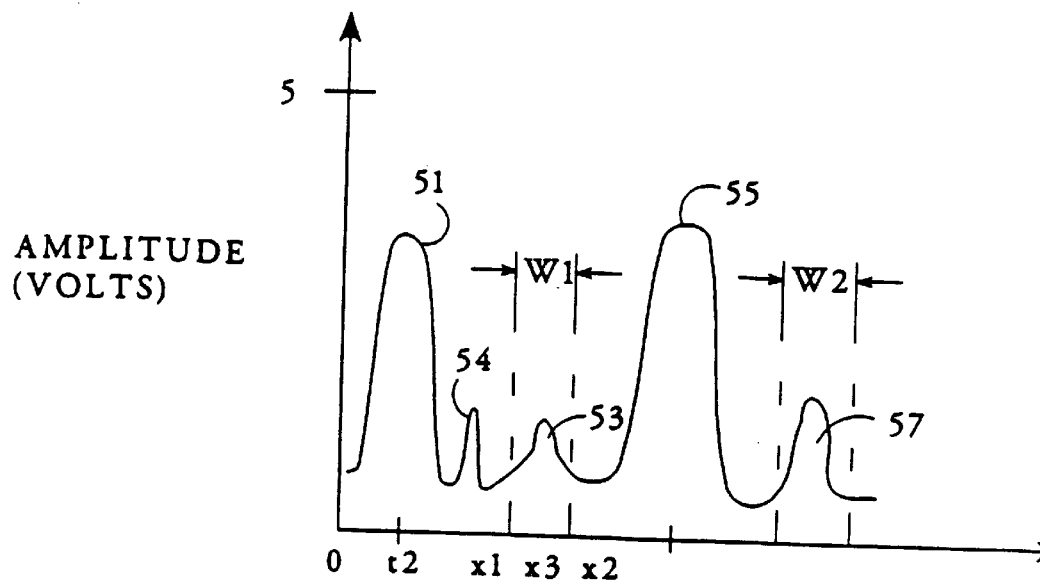
FIG. 3 is a plot of detector signals from unbound and bound fluorescent material.

With reference to FIG. 3, a plot of the detector signal is shown where the horizontal axis is time and the vertical axis is amplitude of the detected signal. As an example, electrophoresis begins at a first time, t=0, and the detector is made operative. At a second time, t3, a relatively large peak 51 is observed, representing free fluorescent labeled marker of a first color. Another signal 54, discussed below, is detected after peak 51. A time later, $t_3$, a weaker signal 53 of the same color is observed. The peak 53 exists in the mid-region of a window, W1, between X1 and X2. The existence of window W1 is established by the labeled binding agent signal 51. Peak 53 is within window W1 and is recognized as a signal from the complex. Peak 54 is not within window W1 and is treated as a false positive or artifact, after being checked to determine whether the signal is not mistaken for the labeled binding agent signal 51. A search of all signals is made to determine the most logical positions for free and bound fluorescent substances. If no signal is found in time window W1, the absence of target analyte is inferred. Each window W acts as a time domain filter, allowing discrimination of spurious fluorescent signals and noise. Note that all signals are recorded and signal discrimination occurs after recording by analyzing recorded data. Even though gel to gel characteristics may vary, the present invention has immunity to most variations because the complex and labeled binding agent traverse the same path.

The ratio of the two signals represented by the area under the peaks 51 and 53 represents an estimate of the ratio of a complex to labeled binding agent after normalizing data relative to calibrations, assuming good binding efficiency. A further time later, another large peak 55 is observed. This represents another fluorescent binding agent. This defines another time window W2 at a subsequent time and a lesser peak 57 is measured in the window. This is taken to represent a complex. Again, the ratio of complexes to free dye is computed and once again the target analyte associated with the second dye may be estimated in concentration.

Figure 4:
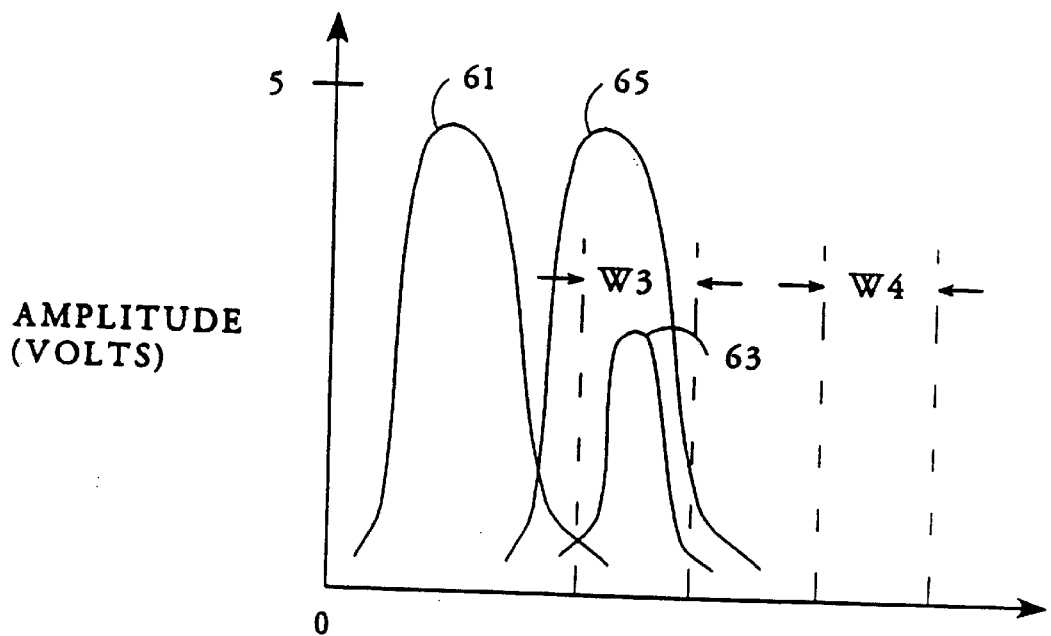
FIG. 4 is a plot of overlapping detector signals of different wavelength from unbound and bound fluorescent material.

It is possible for the peaks to overlap each other as shown in FIG. 4. Here, the labeled binding agent substance peak 61, having a relatively large amplitude, overlaps the second peak 65 of similar amplitude in a test where two different fluorescent substances were used. The second peak 65 is the second free fluorescent substance signal. However, because different colors are used, as separated by the filter 43 in FIG. 1, the two peaks may be separately observed. Peak 61 establishes the time window W3 where a peak 63, representing a bound fluorescently labeled binding agent of a color which is the same as that associated with the unbound peak 61, occurs totally within the second peak 65. Nevertheless, because of the filter 43, peak 63 may be spatially and optically differentiated from peak 65. The ratio of bound to unbound signal amplitudes appears to be about 2:1. The corresponding molecular amounts of complex and labeled binding agent are estimated to be in the same ratio. For the peak 65, a time window W4 is established, but no fluorescent signal is found within the window and so the absence of target analyte is inferred.

Figure 5:
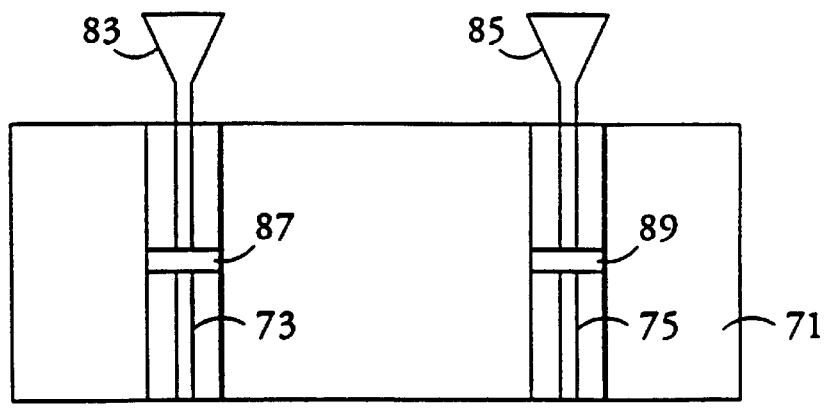
FIG. 5 is a top view of a multiple lane gel arrangement for electrophoresis.

With reference to FIG. 5, a multiple lane electrophoresis sheet gel is shown. The sheet 71 is provided with two lanes 73 and 75. Each of the lanes has a respective well 83 and 85 and a respective slit image 87 and 89. The two lanes are constructed similarly, with the spot image locations in the same position. Lane 73 is used to run a calibrated amount of target analyte, a known amount of free fluorescently labeled binding agent, and a fixed amount of a second labeled marker. In lane 75 an unknown amount of target analyte is run with free fluorescent labeled binding agent and the same fixed amount of the second labeled marker. The two lanes may be compared after normalization of peak area between lanes using the peak area of the second labeled marker to determine the amount of unknown analyte in lane 75. For greater accuracy, multiple runs may be made in lane 73 of various amounts of target analytes so that many ratios may be stored in a memory. A ratio from a run of an unknown amount of target analyte may then be looked up and compared with known ratios, with the best match indicating the amount of target analyte.

Figure 8:
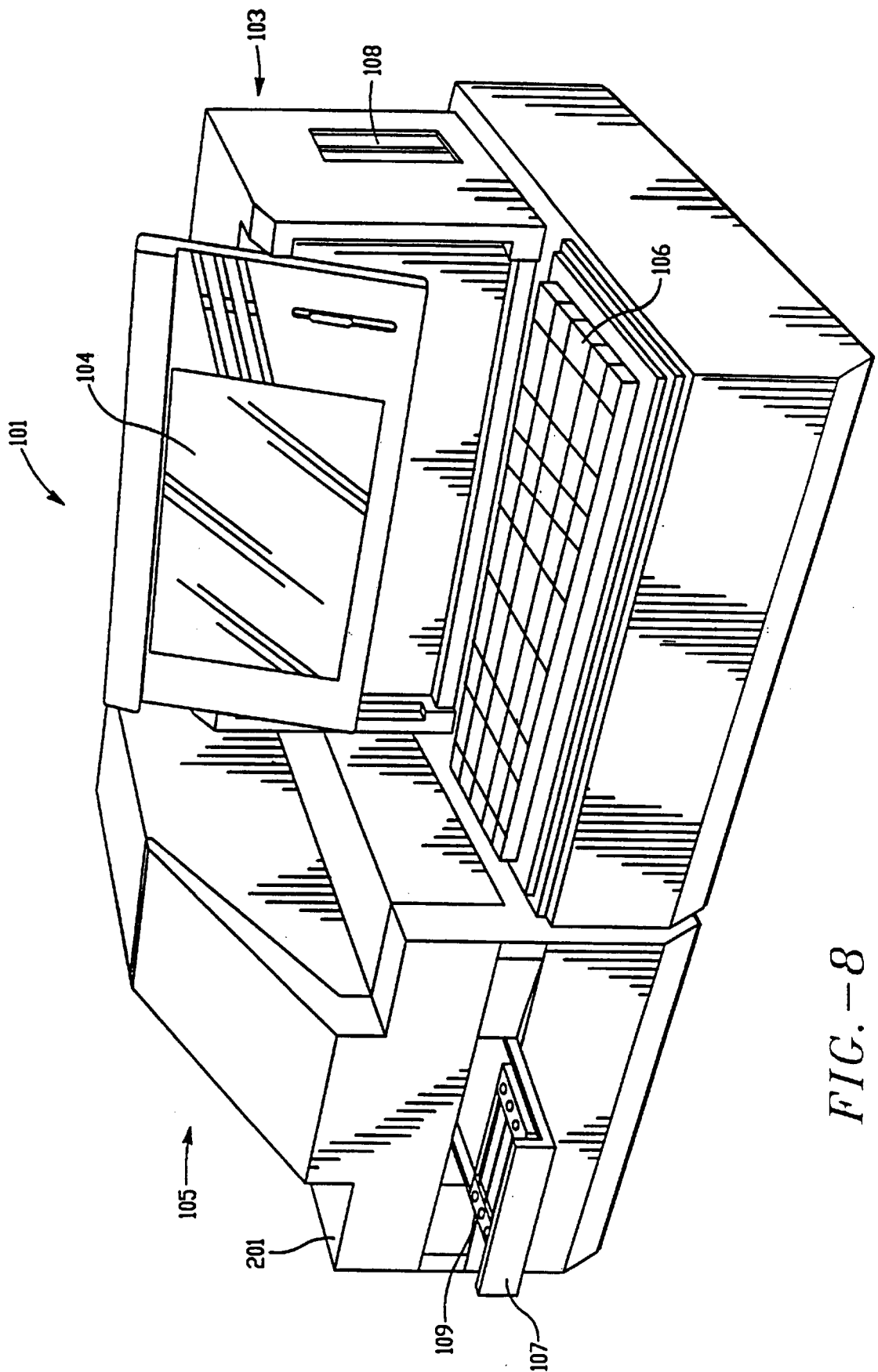
FIG. 8 is a front perspective view of the differential separation assay instrument.

A preferred apparatus for practicing the invention is set out in FIGS. 8–11a and b. With reference to FIG. 8, measurements are made with the instrument 101 which has two main modules, a computer module 103, serving to log and display data, and a measurement module 105, serving to receive samples and subject the samples to testing and measurement in accord with the procedures disclosed herein. Computer module 103 is a standard PC of the 386 or 486 MS-DOS kind, running familiar software suitable for manipulating numbers, such as Excel or Lotus spreadsheets. A display device 104, a keyboard 106 and a disk drive 108 are normal input/output devices associated with the computer. Keyboard 106 is used for signalling commands to the measurement module, such as start, stop, repeat, and so on. The measurement module 15 includes a U-shaped frame 107 for receiving an electrophoresis cartridge 109 and internal optics and electronics covered by the shroud 21. Once a cartridge 109 is placed on frame 107, the frame is pulled under the shroud for the measurements disclosed herein using a signal from keyboard 106.

Figure 9:
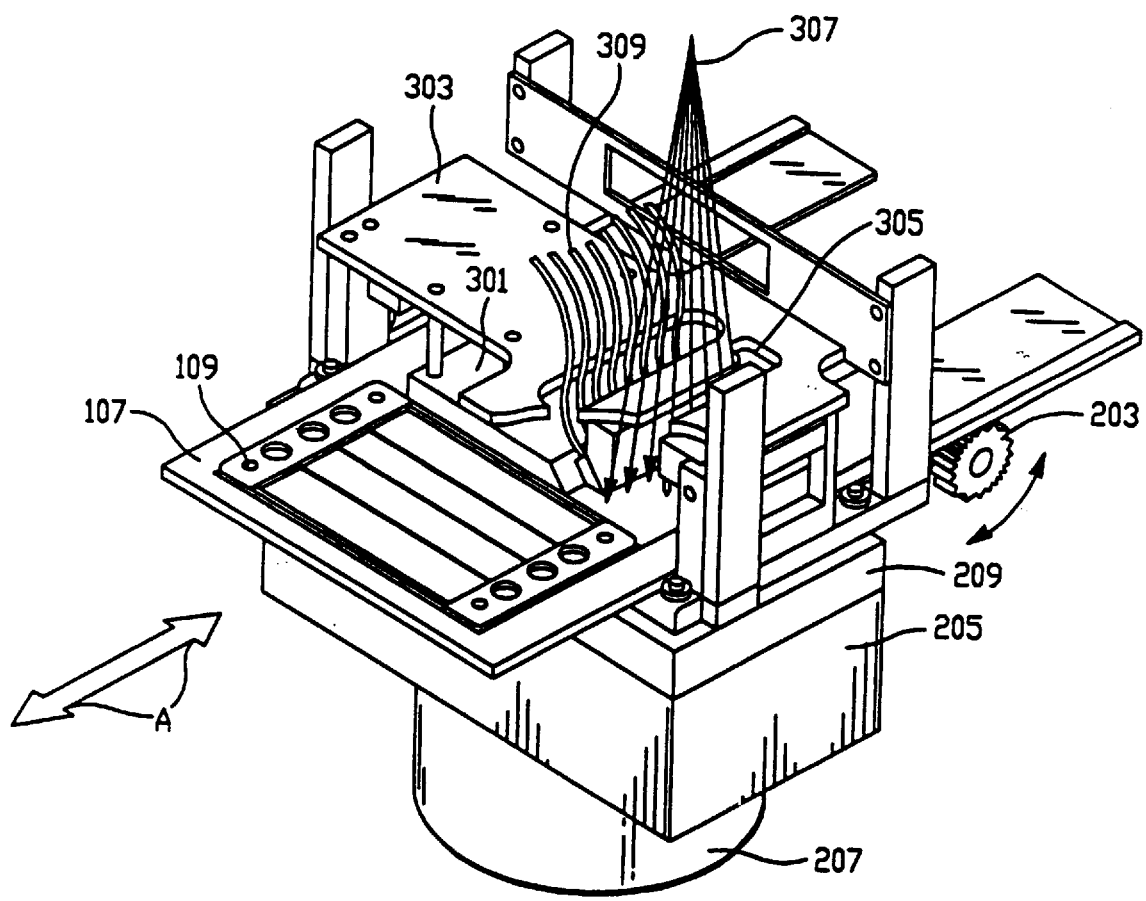
FIG. 9 is a front perspective view of the operating components of the differential separation assay instrument of FIG. 8.

Principal features of the measurement modules are shown in FIG. 9. Frame 107, shown without a protective lip apparent in FIG. 8, supporting electrophoresis cartridge 109, is moved by a pinion gear 203, in the direction indicated by arrows A, to a position wherein the cartridge rests over a Peltier device 205, including a fan within housing 207. The Peltier device is a commercially available refrigeration apparatus which chills a metallic mass 209 of good thermal conductivity, such as an aluminum block, to a temperature suitable for electrophoresis measurements of a particular media. The mass 209 is kept in thermal contact with cartridge 109 by means of a movable pressure plate 301 which is supported from a slotted plate 303 to apply downward pressure on opposed edges of cartridge 109. The pressure plate 301 and the slotted plate 303 are moved downwardly by means of a spring biased actuator, thereby forcing the cartridge 109 into thermal contact with metallic mass 209 with downward force transferred to the cartridge at edges of the cartridge which are supported by frame 107.

A first slot 305 in slotted plate 303 admits a scanning beam 307 which is directed onto a locus of spots on the cartridge, described below. Light scattered, reflected or fluorescing from the impinging light is directed back into optical fibers 309, one fiber corresponding to each beam spot in the locus of spots. Each of the fibers leads to a single optical detector which is always on. The detector output is synchronized with the beam position so that a single fiber is identified as the one providing the optical signal at the detector at any particular time.

Figure 10:
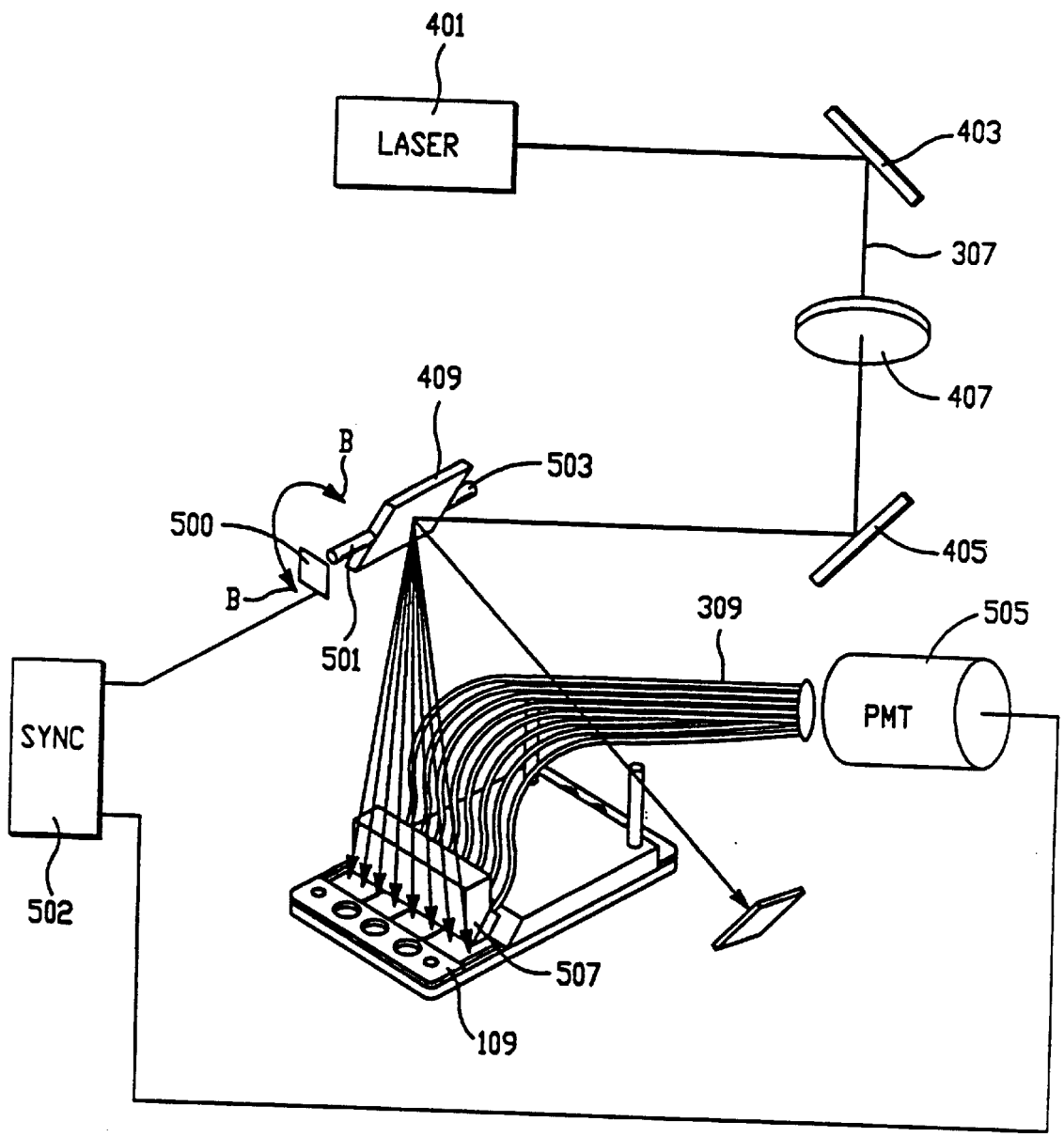
FIG. 10 is a schematic drawing of the optics of the differential separation assay instrument of FIG. 8.

In FIG. 10, incoming light is seen to originate at laser 401, which is a 5 mw helium-neon (HeNe) laser, or a laser of any appropriate wavelength. The beam 307 has its path folded by mirrors 403 and 405, while the beam is collimated by optics not shown and focussed by a lens 407 to form a small spot on a scanning mirror 409. The mirror 409 is located sufficiently close to cartridge 109 that beam spots on the cartridge will not be significantly out of focus. Mirror 409 is rotated about a scanning axis in steps, defined by pivots 501 and 503 for mirror motion indicated by arrows B. A motor, 500, steps the mirror in discrete angular amounts of a few degrees per step starting from a home position at an edge of the support frame where an optical detector is located. A beam scan always starts from the home position and the beam is stepped by known angular amounts to create a limited number of spots at desired locations on a cartridge. The number of steps is counted by an electrical counter, which is a beam synchronizer 502, so that the beam position is known at all times. In this way, the beam position can be synchronized with the detector 505, a photomultiplier or PMT tube which receives light from the optical fibers 309 which are gathered in a bundle. A lens or lenses and a filter, not shown, may be used to optimize coupling between the fiber bundle and the PMT 505. The filter reduces spurious light. At the opposite end of the fibers, a holder block 507 is used to secure each optical fiber in a desired location and to space each fiber very close to the locus of spots where the incoming beam will impinge.

Figure 11A:
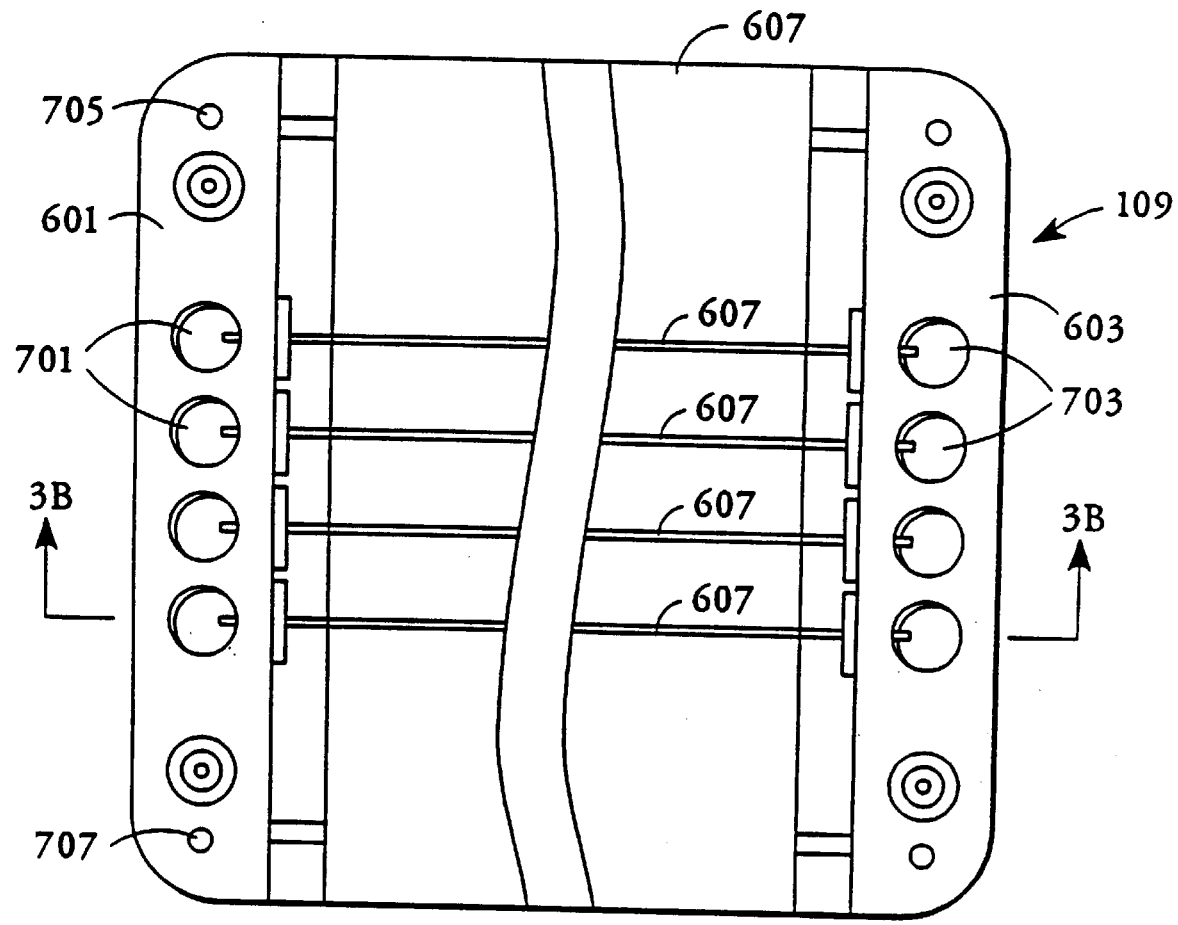
FIG. 11a is a top plan view of an electrophoresis cartridge used in the instrument of FIG. 8.
Figure 11B:
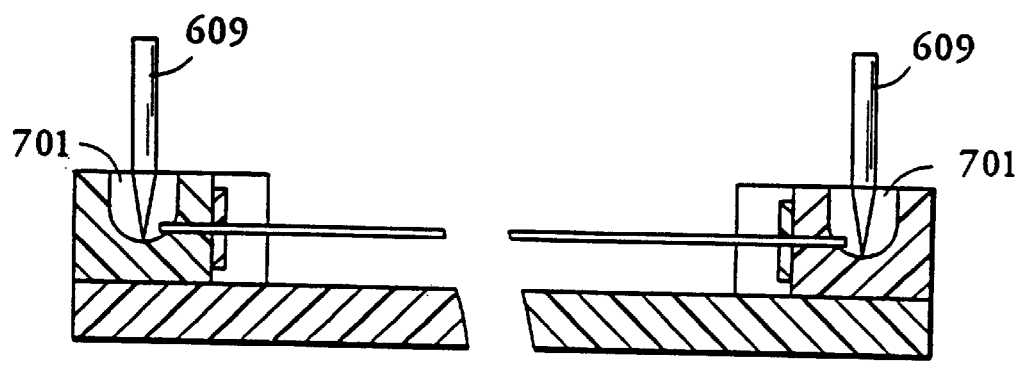
FIG. 11b is a sectional view of the cartridge of FIG. 11a through an electrophoresis channel.

In FIG. 11a, a cartridge 109 is seen to include opposed edges 601 and 603 having apertures 701 and 703 partially extending into the edges. These apertures are known as wells where fluid samples are placed. A fixed amount of labeled antibody is dispensed in the reaction well at one end of the cartridge 109. The antibody may be labeled with a fluorophore which can be excited by light such as light having a wavelength of 633 nanometers (nm). The cartridge can be labeled with a bar code which contains information on the lot to lot variation of the particular antibody preparation used. The same information could also be included on a separate document, sometimes called a lot card, which is shipped with the cartridge. This information can be used to normalize the measurements arrived at using the cartridge. Additional apertures 705 and 707 may be used as detents to index the location of the cartridge in the support frame. Between opposed cartridge edges, slightly above a heat conducting plate 605, are very thin capillary tubes 607 having open ends which extend into the wells 701 and 703 for communicating with any fluid in the wells. The capillary tubes are clear, low reflection material or treated with a coating for low reflection. The tubes have a diameter suitable for electrophoretic migration of a sample in view of the viscosity of the sample. A precisely known aliquot of a sample analyte is applied into the reaction well. After the labeled antibody and sample analyte are combined, the labeled antibody reacts with the antigen which is specific to the labeled antibody to form an antigen/antibody complex or immune-complex. This immune-complex is also fluorescent since the fluorophore is still active in the immune-complex. An amount of the immune-complex is transferred to and migrates across the volumetric capillary 607 whose cross-sectional area is known. The capillary can have dimensions such as 100 micrometers ($\mu$m) round by 30 millimeters (mm) in length. In the locus of beam spots mentioned previously, one beam spot is provided for each capillary tube so that the number of angular steps of the beam needs to at least equal the number of capillary tubes and must be such that the beam lands squarely on a capillary tube for possibly exciting a response from a fluid in the capillary. In FIG. 11b, electrodes 609 and 709 are seen to extend into apertures 701 and 703 in order to make contact with fluid in the well and migrating between the opposed electrodes under the influence of an electric field. In operation, the electrodes come into contact with the wells at the same time a pressure plate clamps the cartridge in place as described above. Electrical potential differences between the electrodes 609 and 709 creates a strong electric field within solution inside the capillary 607 and causes electrophoretic migration along the separation medium in the capillary tubes. After separation is complete, the capillary is scanned with a beam from the HeNe laser. The beam 307 repetitively scans a locus of spots transverse to the length of the capillaries, with a spot falling on each capillary and passing into its center where it illuminates fluid sample material under electrophoretic migration. Fluorescent light emitted from the sample falls upon an end of a nearby optical fiber and the light is guided back to the PMT. After the entire capillary is scanned, and a complete measurement of the fluorescent image is made and stored in the instrument's memory. This image is then subjected to several types of data analysis.

The apparatus of FIGS. 8–11 can also be used to perform different and distinct separation techniques which rely on different characteristics, such as isoelectric focusing. In this distinct separation process, the immune-complex solution can be diluted with a precisely known amount of ampholyte solution. The composition of the ampholyte solution is designed to just span the pH regions of the isoelectric points of the labeled antibody and the immune complex. The high voltage or potential developed within the capillary causes the ampholytes to move immediately to their isoelectric points with the complex and the labeled antibody then moving to their respective isoelectric points. The isoelectric points unique to these chemicals can be determined beforehand during product development.

One of the advantages of the present invention is that analysis of peaks representing bound and free dye can be computed before electrophoresis is complete, i.e., before the migrating substances reach the distant high voltage electrode. Another advantage is that the present system uses only a single lane of an electrophoresis apparatus so that gel to gel non-uniformities are nulled. It is possible to use a second lane in an electrophoresis device as a reference or calibration, but such calibrations may be done beforehand and results stored in a memory. It is also possible to use a second or third or fourth lane for additional analytes of interest creating panels of relevant analytes. In the prior art, analysis of target analytes usually requires completion of the electrophoresis and subsequent analysis by a plurality of stains, colored or fluorescent substrates, etc. Using the present invention, the analysis may be done in real time as soon as sufficient separation exists between the bound and free fluorescent material. Such a separation can be at a point which is only twenty-five percent or thirty-three percent of the length of a lane. Once a point is found where adequate separation exists, the image of the slit or pinhole is positioned at that location and then all measurements are made from there. It is also to be noted that this is an open-ended electrophoresis system, i.e., there is no need to stop the electrophoresis at a defined point to get all materials "on scale." Materials that migrate slowly can be detected just as well as fast moving target analytes. Amplitude thresholds may be used as further discrimination against noise and artificial signals.

To discriminate between two or more target analytes in the same gel lane, individual specific labeled binding agents for each analyte which have different fluorescent wavelengths can be used, so long as filter 43 in FIG. 1 can adequately resolve the different wavelengths. Multiple tests can be run simultaneously, each test associated with a particular wavelength. The total integrated fluorescence can be used to check the quality of the assay. The quality of the assay can be characterized by using data gathered from an initial series of cartridges. For example, the first thirty cartridges can be sufficient. Included in this characterization is data which will be used in an on-going basis to check the assay for quality control (QC). The total integrated fluorescence is used to check for the correct chemical preparation of the sample.

The entire fluorescent image is integrated and then monitored for changes run to run. This integrated fluorescence is proportional to a variety of factors including: (i) the total amount of fluorescent material loaded into the reaction well; (ii) the length of the capillary; (iii) the accuracy of manipulations in the various fluid handling steps; and (iv) the photometric response of the instrument.

The first thirty or so cartridges can be used to determine the typical response of the system to a correctly prepared cartridge. This minimizes the effects of factors (i), (ii) and (iii). The effect of factor (i) is minimized by coding a normalization factor onto the cartridge's bar-code or lot card. This factor corrects for the lot to lot variation in the amount of fluorescent material in the reagent cup. FIG. 12 is a flow chart illustrating the normalization factor for factor (i). A sample cartridge from a lot would be run 810 through the measuring apparatus. The cartridge is scanned 812 for the fluorescent label signal $I_f(x)$ over the time intervals from zero to L. Values for the fluorescent standard $I_s$ for the expected amount of fluorescent material, and the background brightness $I_B$ are read 814 into the measuring apparatus. The total fluorescence is computed 816 by taking the integral of the difference between the scanned label and the background brightness over the time intervals from zero to L. The integral is then divided by the difference between the fluorescent standard and the background brightness to arrive at a total fluorescence value $I_T$ which is then used to normalize 818 the photoresponse measurements of this lot of cartridges.

The effect of factor (ii) is also removed by coding a normalization factor onto the bar-code for the cartridges. This factor corrects for lot-to-lot variation in cross-sectional area and capillary length. The effect of factor (iii) is minimized by averaging over the first thirty cartridges. A moving window based on the previous thirty cartridges can be used afterwards. Individual cartridge results may be removed from this average if they lie more than two standard deviations from the mean. This type of charting and range setting is commonly used in the form of a Levey-Jennings plot. This enhances the remaining effect of factor (iv), the expected photometric response of the instrument.

Each sample run then has its integrated fluorescence computed and corrected for lot-to-lot variations. The antigens in a patient sample is contacted 820 with the labeled antibodies and separation medium of the cartridge. The separation procedure is then performed 822 and the patient sample is then scanned 824 for its fluorescent signal $I_f(x)$. Values accounting for the capillary lot information $I_V$ are then read 826 into the measuring apparatus. The measured fluorescent signal $I_C$ from the scanned sample can be determined from the following relationship:

$$I_c = \frac{\int_0^L (I_f(x) - I_B) dx}{(I_S - I_B) I_T I_V}$$

This integrated fluorescence is compared 832 with the expected photometric response of the instrument, which is represented by the mean and standard deviation "σ" of the last thirty cartridge samples 830. If a particular sample has an integrated fluorescence that is more than two standard deviations from the expected photometric response of the instrument, it is assumed that this sample was misprepared in some fashion and it is flagged 834 as unsuitable and out of quality control bounds. Another sample can then be assayed. Otherwise the measured result of the assay is reported 836.

Figure 15:
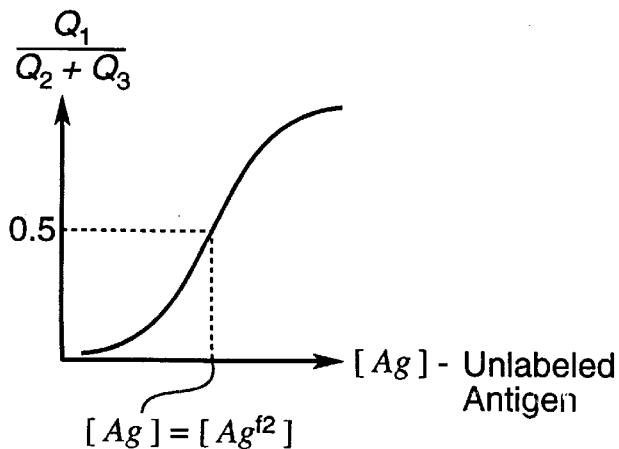
FIG. 15 shows an assay standard curve established for a two color competitive assay in accordance with the invention.
Figure 16:
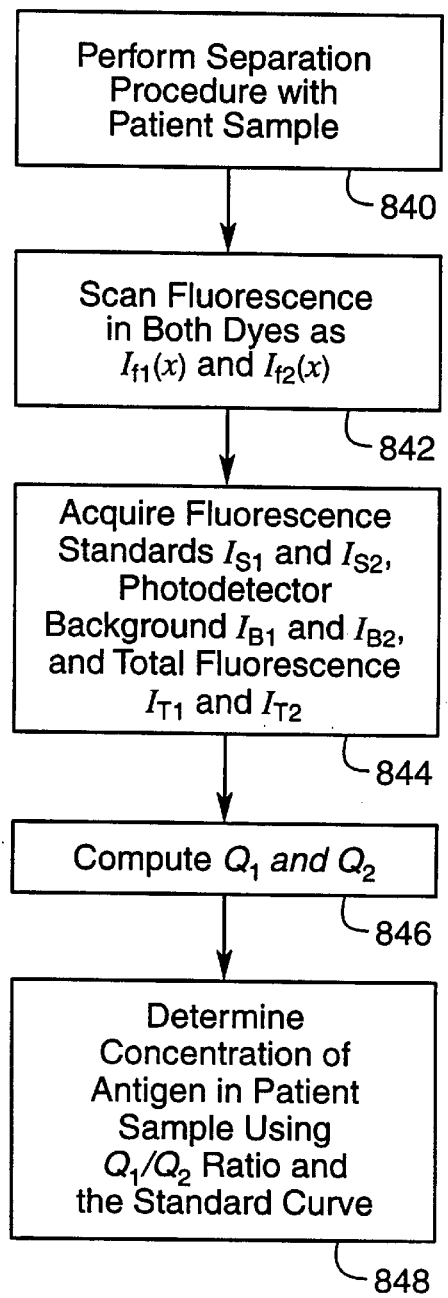
FIG. 16 shows a flow chart for a two color competitive assay technique in accordance with the invention.

Another embodiment of the invention assays an antigen present in the sample analyte based on a competition reaction between the sample antigen and a separate quantity of that antigen which has been labeled. FIGS. 15 and 16 refer to a two color competitive assay embodiment of the invention. In the competitive assay, the reagent well is loaded with two reagents, each one labeled with a different fluorophore, f1 and f2, respectively. One reagent is a fluorescently labeled antibody specific to an antigen of interest. The antibody is labeled with fluorophore f1 which for this system with HeNe laser excitation could be a Cy5™ dye. The Cy5™ dye is a reactive cyanin with fluorescence characteristics similar to allophycocyanin having a molecular weight less than one-thousand. It is a succinimidyl ester provided as a dried dye having an absorption maximum at 652 nanometers (nm) and an emission maximum of 667 nm to about 800 nm, and is available from Biological Detection Systems, Inc. of Pittsburgh, Pa. The other reagent is the antigen to which this antibody is specific, however, this antigen has been conjugated with fluorophore f2. For a system with HeNe laser excitation, the second fluorophore could be a Cy5.5™ dye. Cy5.5™ dye has an absorption maximum at 652 nanometers (nm) and an emission maximum of 667 nm to about 800 nm, and is also available from Biological Detection Systems, Inc. of Pittsburgh, Pa. When the two reagents are combined with the sample, a competitive assay progresses. The term "competitive" refers to a situation where two different forms of the antigen are competing for reaction with the antibody. This competition reaction can occur under three different types of conditions.

In the assay condition of no sample antigen being present in the sample, the only complex formed will be that of the labeled antigen and the labeled antibody. This complex contains two fluorophores. Upon presentation to the cartridge this reaction mixture will form two different peaks: one of the dual fluorescently labeled complex, and the other of the excess fluorescently labeled antibody.

In the assay condition of a high concentration of antigens in the sample (far more than provided as labeled antigen) most of the immune-complexes will be formed with sample antigen rather than the fluorescently labeled antigen; this is due to the sheer excess of sample antigen. Upon presentation to the cartridge this reaction mixture will form two different peaks: one of the fluorescently labeled antigen, and the other of the excess fluorescently labeled antibody.

In an intermediate third assay condition for a sample containing antigen between the two extremes discussed above, a dynamic equilibrium exists so that a portion of the complexes are formed with sample antigen and the remaining complexes are formed with fluorescent antigen which yields dual fluorescently labeled complexes. Upon presentation to the cartridge this reaction mixture will form 3 peaks: one of the fluorescently labeled antigen complex, one of the dual fluorescently labeled complex, and one of the excess fluorescently labeled antibody.

Figure 14A:
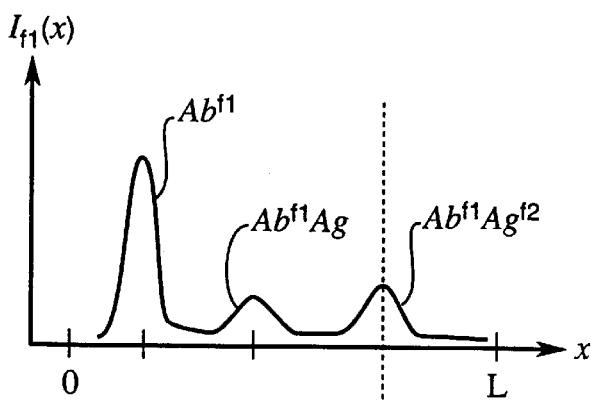
FIGS. 14a and 14b each show a plot of detector signals for two different fluorescent labels in a two color competitive assay in accordance with the invention.
Figure 14B:
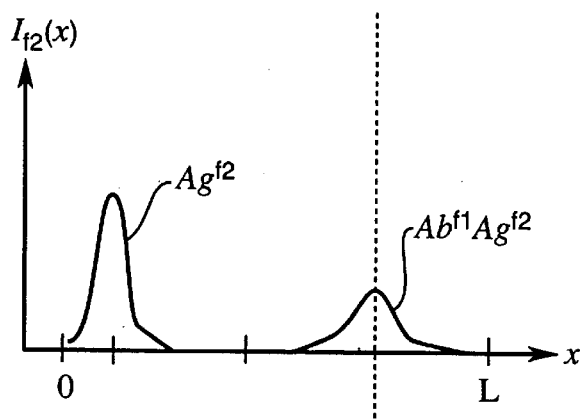

FIGS. 14*a* and 14*b* show separate scans for the fluorescent signals $I_{f1}(x)$ and $I_{f2}(x)$ two fluorophores f1 and f2. In scanning for fluorophore f1, photoresponses for the excess free labeled antibody ($Ab^{f1}$), the complex ($Ab^{f1}Ag$) formed from the unlabeled sample antigen, and the complex ($Ab^{f1}Ag^{f2}$) formed from the labeled antigen standard are detected. In scanning for fluorophore f2, photoresponses for the free labeled antigen ($Ag^{f2}$), and the complex ($Ab^{f1}Ag^{f2}$) formed from the labeled antigen standard are detected. The time during which the dual fluorescent complex ($Ab^{f1}Ag^{f2}$) is detected for fluorophore f1 should correspond with the time during which the dual fluorescent complex is detected for fluorophore f2. This can serve to check on the quality or accuracy of the assay. As shown in FIG. 14*a*, there may be some separation between the single fluorescent complex ($Ab^{f1}Ag$) and the dual fluorescent complex ($Ab^{f1}Ag^{f2}$) because of the additional fluorophore f2.

A quantitation function can be defined as Gaussian to give the best fit of the area under the peaks of the fluorescent signals for a Gaussian distribution. These terms can be denoted as Q1 and Q2, wherein Q1 measures the free labeled antigen and Q2 measures the dual fluorescently labeled complex. The total fluorescence $I_{T1}$ and $I_{T2}$ for each fluorophore f1 and f2 can be determined much as discussed in regard to FIG. 12.

A standard curve, shown in FIG. 15, for the competition reaction can be established based on the relationship between sample antigen concentration [Ag] and the free to the bound labeled antigen ratio (i.e., the ratio of the concentration of fluorescently labeled antigen [$Ag^{f2}$] to the concentration of the dual fluorescently labeled complex [$Ab^{f1}Ag^{f2}$]). The standard curve indicates the response of the ratio of the labeled complex peak with the total integrated fluorescence. This modality normalizes systematic system variations such as small fluid dispense errors, PMT gain drift, laser output drift, lot to lot variations of the reagent chemistry such as F/P ratio and dye QE (quantum efficiency), and so on. A variation of this modality uses a information from the cartridge bar-code or lot card which establishes the moles of labeled antibody present. This term can be used to convert the ratio computed to absolute number of moles of the antigen present. The concentration of fluorescently labeled antigen and the concentration of dual fluorescently labeled complex are determined by integrating the signal of their fluorescent responses.

Turning to FIG. 16, the separation procedure is performed 840 using a patient sample and the results scanned 842 for both dyes. Values accounting for the fluorescent standard $I_{S1}$ and $I_{S2}$, background brightness $I_{B1}$ and $I_{B2}$, and total fluorescence $I_{T1}$ and $I_{T2}$ for each fluorophore f1 and f2 respectively, and capillary lot information $I_V$ are then acquired and read 844 into the measuring apparatus. The quantitation functions Q1, Q2 and Q3 are determined 846 based on the above values and integrating the signal of the fluorescent responses. Q1 measures the free labeled antigen [$Ag_{f2}$], Q2 measures the dual fluorescently labeled complex [$Ab_{f1}Ag_{f2}$], and Q3 measures the complex [$Ab_{f1}Ag$] formed from the labeled binding agent and the sample antigen. The ratio of Q1/(Q2+Q3) and the standard curve are then used to determine 848 the unknown concentration of antigen in the patient sample. Since the amplitude of the photoresponse may be small for the dual fluorescent complex, cross-correlation may be employed as shown below:

$$Q2 = \frac{\sum\limits_{x=0}^{L} (I_{f1}(x) - I_{B1})(I_{f2}(x) - I_{B2})}{\left(\sum\limits_{x=0}^{L} I_{f1}(x) - I_{B1}\right)\left(\sum\limits_{x=0}^{L} I_{f2}(x) - I_{B2}\right)}$$

can be used to further enhance the signal. Other methods will be apparent to those skilled in the art.

EXAMPLE 1

Detection of proteins present in human blood

Creatine kinase is an enzyme present in various mammalian tissue. It occurs in three different forms known as isoenzymes: CK-MM (skeletal), CK-MB (cardiac) and CK-BB (brain). After release from tissue and on circulation in blood the MM and MB forms themselves break down to smaller fragments known as isoforms or subforms. In the event of myocardial infarction, the MB isoenzyme, present in cardiac muscle, is released into plasma. Hence, it serves as a specific diagnostic molecular marker for cardiac ischemia or necrosis. The early and rapid detection of this isoenzyme and its isoforms are very crucial for the diagnosis of myocardial infarction and for initiating thrombotic therapy.

To perform the test, a blood sample is separated into plasma and red blood cells. The plasma is mixed with excess antibody tagged with a fluorescent dye which is directed against CK-MB. The attachment of fluorescent antibodies for a CK assay is known and is described in U.S. Pat. No. 4,353,982 to M. Gomez et al. If CK-MB is present in plasma, an immune complex consisting of CK-MB and fluorescently tagged antibody will be formed. On application of an electric field, the reaction mixture consisting of the fluorescent immune complex and the unreacted fluorescent antibody, will migrate on the gel. Because of charge and mass differences, the labeled intact immune complex will migrate differently than the labeled antibody. The fluorescence associated with bound and free markers will be detected and arrival times measured and recorded. Free marker is identified by a large peak. Any substance within the expected time of the free substance is regarded to be target analyte. Anything else is an artifact.

EXAMPLE 2

Detection of the presence of sexually transmitted diseases

Many sexually transmitted pathogens such as chlamydia, herpes, etc., form lesions in the urogenital area. For detection of these pathogens, samples are taken with a swab directly from the lesion and a number of different types of tests are performed on this extract. These tests include culture and/or immunochemical tests.

After a lesion is sampled with a swab, the swab is treated with a solubilization reagent to liberate micro-organism present. This process will also solubilize target analytes originating from the micro-organisms. This extracted solution will be filtered and reacted with fluorescently tagged antibody so that there is a substantial excess of unreacted tagging substance. The differential assay proceeds as described above.

If the difference between the charge, mass, shape, or combination of these characteristics of the bound and free substances is great, early separation may be expected. The results of electrophoresis are predicted at an earlier time than a complete electrophoresis run.

EXAMPLE 3

Detection of antibody to human serum albumin (HSA)

In the following example, an antibody against HSA is the target substance which is detected by tagging with fluorescent HSA. HSA, Fraction V, was obtained from Sigma Chemical Company (St. Louis, Mo.). Monoclonal anti-HSA was obtained from Biospacific Inc., California. Cy5-labeled HSA was synthesized by the coupling of Cy5 fluorescent dye to HSA (Biological Detection Systems, Inc., 4617 Winthrop Street, Pittsburg, Pa. 15213, This fluorescent substance is the binding agent.

Differential separation assay (DSA) was done as follows: Cy5-labeled HSA (binding agent) was incubated with monoclonal anti-HSA (target) at a final concentration of 400 ng/ml Cy5-HSA and 200 ug/ml anti-HSA in 0.09M Tris, 0.08M borate, 0.25 mM EDTA, pH 8.3. A control sample consisted of Cy5-HSA alone at 400 ng/ml without added antibody. Reactions were performed in 1.5 ml Eppendorf tubes in a total reaction volume of 20 ul. After incubating the samples at room temperature (20° C.) for 30 minutes, 10 ul aliquots were loaded onto 6% nondenaturing (8 cm×10 cm×0.75 mm) polyacrylamide gels (Jule labs) containing 0.9M Tris, 0.8M Borate, 2.6 mM EDTA, pH 8.3. Electrophoresis was performed at 100 V for 40 minutes using a Hoefer Mighty Small SE200 system.

The real time detection of fluorescent proteins during electrophoresis was performed using a He-Ne laser beam focussed at a point 1.3 cm below the wells of the gel. The emitted fluorescence was collected using a photomultiplier (PMT) tube. Data was collected using a Lab-PC from National Instruments (Trademark) (Austin, Tex.) data acquisition board on the IBM-PC and imported into a Microsoft Windows (Trademark) Excel (Trademark) file for analysis and graphics.

Samples containing excess Cy5-HSA were reacted with excess monoclonal anti-HSA and then were loaded onto 6% acrylamide gels. Separation on this gel system is based on charge/mass characteristics of the proteins and more rapidly migrating species migrate past the laser beam earlier than more slowly migrating protein species.

Figure 6:
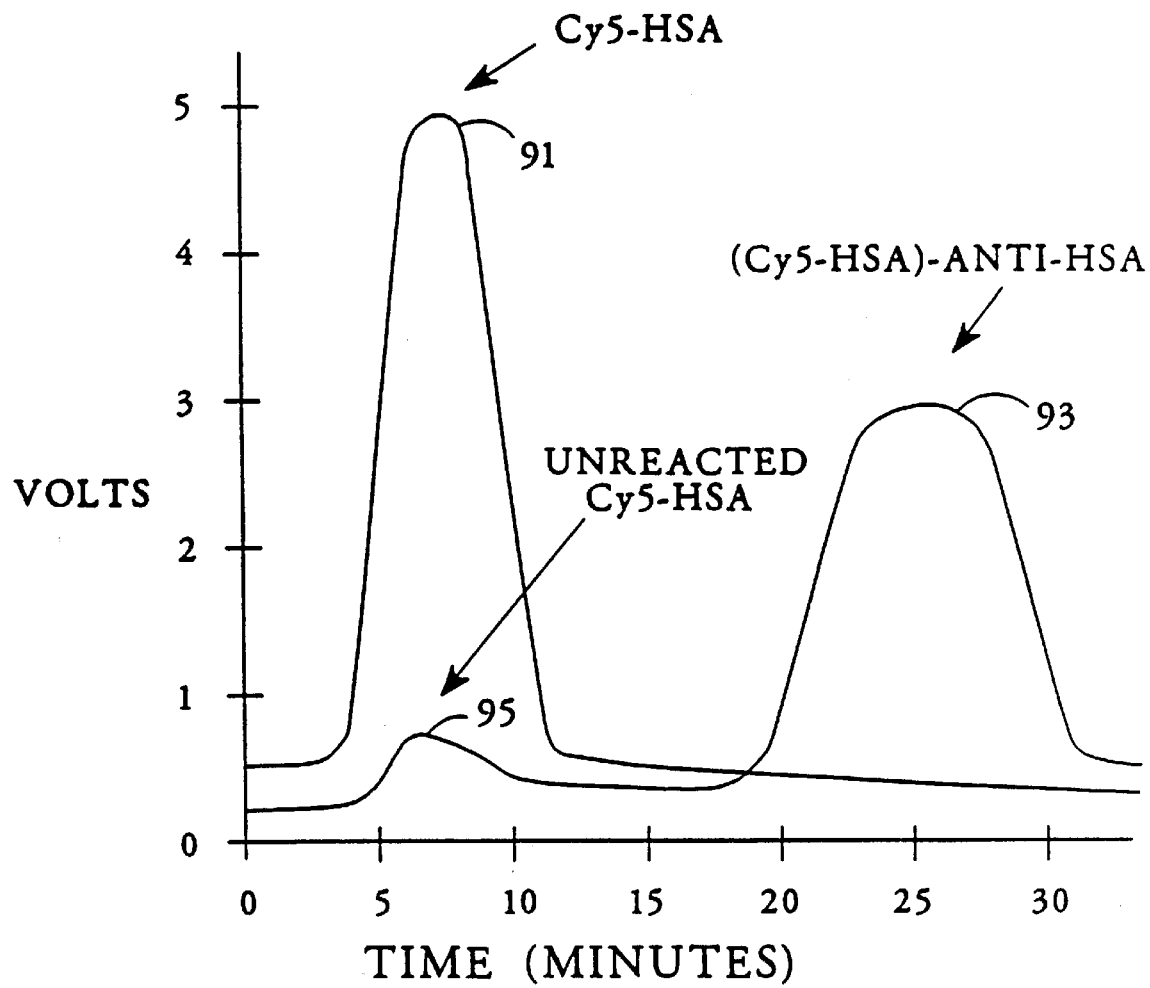
FIG. 6 shows the electrophoretic migration of Cy5 labeled human serum albumin (HSA) and Cy5 labeled human serum albumin complexed with an antibody.

With reference to FIG. 6, the Cy5-HSA peak 91 migrates past the laser beam at approximately 8 minutes. This is a first calibration run to establish a time for free Cy5-HSA. The immune complex consisting of Cy5-HSA-Anti-HSA, on the other hand, has a peak 93 which migrates past the laser spot at 25.5 is a second calibration run minutes. This example demonstrates that the relevant time window for this pair of binding agent (Anti-HSA) and fluorescent tag (Cy5-HSA) is 17.5 minutes in this separation medium. The 8 minute peak 91 defines the time window in which to search for the Cg5-HSA peak of the inmmune complex Cy5-HSA-Anti-HSA in the second calibration run. Peak 95 lies within this window and is identified as the residual uncomplexed labeled Cy5-HSA.

EXAMPLE 4

Detecting mediators of septic shock

Septic shock is the most common cause of death in a medical-surgical intensive-care unit. Mortality rates range from 40% for early phase sepsis to more than 70% for refractory septic shock. Septic shock develops in a cascade fashion.

Bacterial antigens (including endotoxin) activate local tissue macrophages, blood monocytes, and serum complement. Local complement activation induces (directly and indirectly) migration and activation of blood neutrophils—as do the macrophage and monocyte activation products (which include interleukin-1 and tumor necrosis factor). In addition, activated macrophages and lymphocytes produce (again directly or indirectly) molecules that stimulate the endothelial cells to produce more neutrophil chemotactic factors. Several of these cytokines increase endothelial permeability. This in turn promotes blood-neutrophil adhesion and migration.

Once activated, the neutrophil releases cytolytic enzymes and reactive oxidants. Chronic exposure destroys the local endothelial vasculature. Such persistent local damage impairs vascular integrity to such an extent that hemodynamic homeostasis cannot be restored. Death is the result.

Unstimulated neutrophils constitutively express lectin adhesion molecules (LECAM-1). The passive interaction of these molecules with the endothelial cell ligands, intercellular adhesion molecule-1 (ICAM-1), and endothelial-leukocyte adhesion molecule-1 (ELAM-1) induces neutrophil activation and transmigration. Transmigration is promoted by the up-regulation and interaction of neutrophil-specific integrins with endothelial ICAM-1 and ELAM-1. Tumor necrosis factor, interleukin-8, lipopolysaccharide (LPS), gamma interferon and interleukin-1 can stimulate endothelial cells to express neutrophil adhesion molecules.

Endogenous mediators of sepsis are listed in Table 1.

Table 1

Adhesion molecules
  (ELAM-1, ICAM-1, VCAM-1)
Beta-endorphin
Bradykinin
Coagulation factors (including fibrin, thrombin)
Complement fragments (C3a, C5a)
Elsosenoids (leukotrienes B. C. D. E. thromoxane $A_2$, prostaglandins $E_2$)
Endothelin-1
Endothelin-derived relaxing factor
Interferon 5
Granulocyte-macrophage colony stimulating factor
Interleukins (1, 2, 4, 6, 8)
Macrophage-derived procoagulant and inflammatory cytokine
Myocardial depressant substance
Plasminogen activator inhibitors
Platelet activating factor
PMN leukocyte products
  (toxic oxygen radicals, proteolytic enzymes)
Serotonin
Transforming growth factor beta
Tumor necrosis factor A
Vascular permeability factor These mediators to sepsis can be conveniently and rapidly detected by methods and test kits of this invention. In particular, it is important to rapidly detect LPS, tumor necrosis factor (TNF), interleukin-1, interleukin-8 and gamma interferon to evaluate the progress of septic shock. Lipopolysaccharide (LPS) and monoclonal antibodies to LPS are described in U.S. Pat. No. 5,093,235. Monoclonal antibodies to TNF interleukin 1 and 8 and γ interferon are described in *Current Protocols in Immunology*, supra.

Following the procedures in Example 3, except the antibody is labeled and the cytokine is the analyte, LPS, interleukin-1, interleukin-2, TNF α, and gamma interferon are determined.

EXAMPLE 5

Preparation of second labeled marker

Bovine serine albumin is dissolved at about 1 mg/ml in 50 mM phosphate buffered saline PBS. This bovine serum albumin solution is reacted with a solution of carboxymethylindocyanine succinimidyl ester in accordance with the procedure in *Cytometry* 11: 418–430 (1990). A kit for such labeling is sold by Biological Detection Systems, Inc., 4617 Winthrop Street, Pittsburgh, Pa. 15213.

Figure 7:
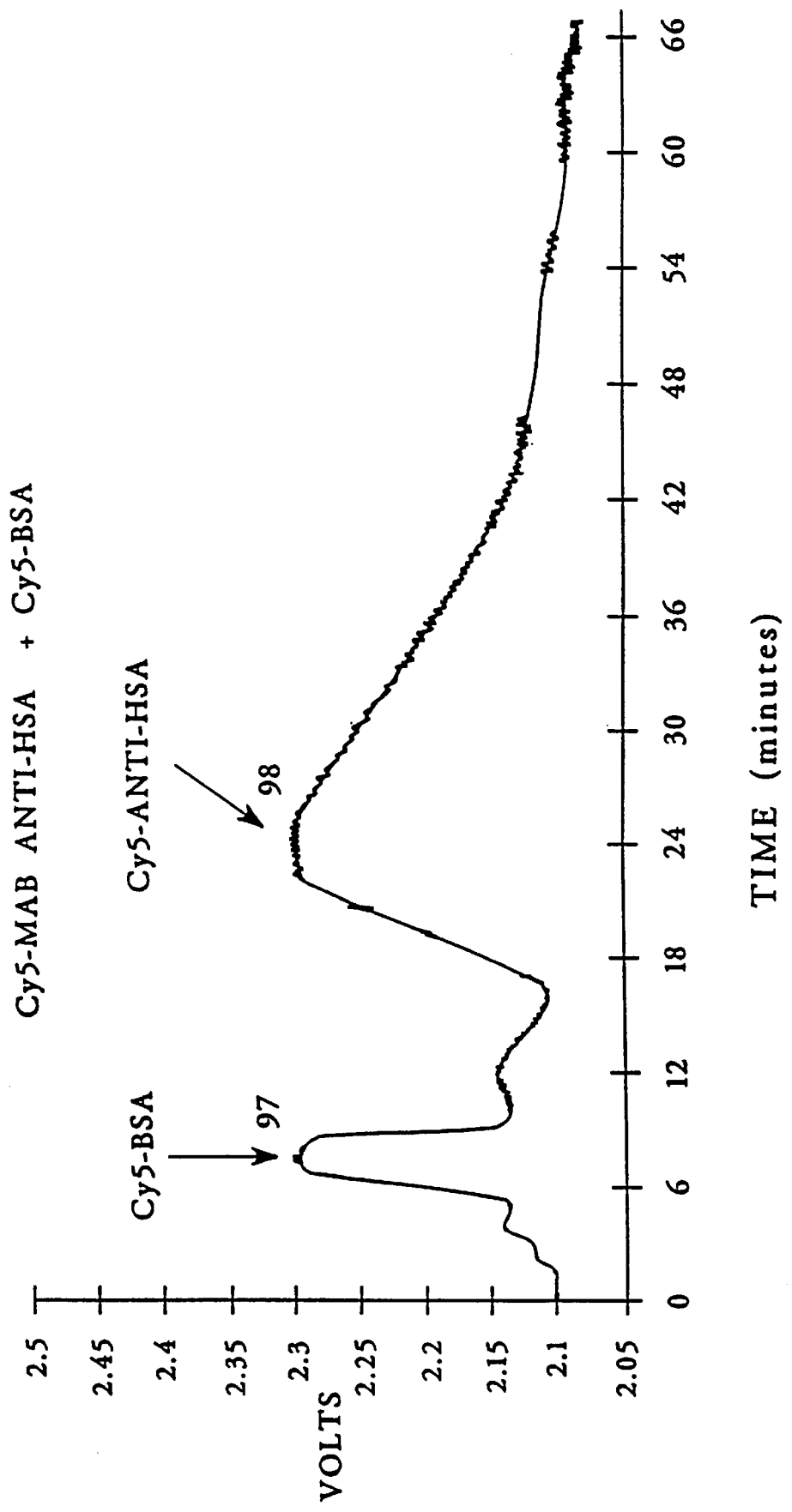
FIG. 7 shows the electrophoretic migration of Cy5 labeled bovine serum albumin (BSA) as a second labeled marker and Cy5 labeled anti-HSA.

FIG. 7 shows the differential migration of Cy5-BSA peak 97 and Cy5-labeled monoclonal anti-human serum albumin peak 98. Thus, Cy5-BSA is a suitable second labeled marker.

The above examples are intended to illustrate the invention and not to limit it in spirit or scope. While several particular forms of the invention have been illustrated and described, it will also be apparent that various modifications can be made without departing from the spirit and scope of the invention.

What is claimed is:

1. A method for detecting an analyte in a test sample comprising:
   a) labeling a specific binding agent with a detectable label, wherein the labeled binding agent specifically binds to the analyte to form a complex;
   b) providing a separation medium on which the labeled binding agent and complex migrate at different velocities during electrophoresis;
   c) contacting the test sample with an excess amount of labeled binding agent to produce a reaction mixture containing the labeled binding agent and the complex;
   d) separating the labeled binding agent and complex by applying the reaction mixture to the separation medium to separate the complex from the labeled specific binding agent by electrophoresis;
   e) measuring and recording the migration of the labeled binding agent and the complex as a function of time between at least two reference points on the separation medium;
   f) defining a time window using predetermined migration values of the labeled binding agent and complex between at least two reference points on the separation medium; and
   g) comparing the recorded migration of the complex with the time window as a time domain filter to determine the presence of the analyte, wherein finding the complex within the time window indicates presence of the analyte.

2. A method according to claim 1 wherein the analyte is an antigen and the labeled binding agent is a labeled antibody.

3. The method according to claim 2 wherein the analyte is in a mammalian body fluid.

4. The method according to claim 2 wherein the antibody is a monoclonal antibody.

5. A method according to claim 1 wherein the analyte is a cytokine and the labeled binding agent is a fluorescent dye labeled monoclonal antibody or receptor to the cytokine analyte.

6. A method according to claim 5 wherein the analyte is a lipopolysaccharide (LPS), tumor necrosis factor or an interleukin.

7. The method of claim 1 wherein the analyte is selected from the group consisting of creatine kinase and its isoenzymes and isoforms.

8. A method for measuring the concentration of an analyte which forms a complex with a specific binding agent in a test sample comprising:

(a) labeling the specific binding agent with a detectable label;

(b) contacting the test sample with an amount of the labeled binding agent in excess of what will react with the analyte so as to form a complex with analyte, and produce a reaction mixture containing the labeled binding agent and the complex;

(c) providing a separation medium on which the labeled binding agent and complex migrate at different velocities;

(d) separating the labeled binding agent and complex by applying said reaction mixture to the separation medium for separation by electrophoresis;

(e) measuring and recording the migration of the labeled binding agent and the complex as a function of time between at least two reference points on the separation medium by detecting the label wherein the recorded migrations are characterized as peaks;

(f) defining a time window statistically using predetermined migration times for the labeled specific binding agent and complex between at least two reference points on the separation medium; and (g) comparing the migration of the complex with the time window as a time domain filter to determine the presence of the analyte, wherein detecting the labeled complex within the time window indicates presence of the analyte;

(h) measuring the area under each peak of the detected label within the time window; and (i) normalizing the areas under each peak of the labeled complex to determine the concentration of the analyte.

9. The method according to claim 8 wherein the labeled binding agent and complex migrate at different rates along the same path in the separation medium.

10. The method according to claim 8 wherein the labeled marker is a fluorescently labeled molecule.

11. The method according to claim 8 wherein the label has a fluorescent standard, the measuring step uses a photodetector to detect the fluorescent label, and further includes the steps of:

reading the fluorescent standard of the label and a background brightness of the photodetector;

integrating the difference between the detected fluorescent label for the binding agent and the background brightness over a predetermined number of time intervals; and dividing the integrated difference between the detected fluorescent label and the background brightness by the difference between the fluorescent standard and the background brightness to arrive at a normalized factor; wherein the normalized factor is used in the step of normalizing areas under each peak.

12. The method according to claim 8, wherein the label is fluorescent and a photodetector is used to detect the fluorescent label, the method further comprising the steps of:

determining the total integrated fluorescence of the test sample;

determining an expected photometric response of the photodetector based on previous test samples measured; and recording the area under the peak for the complex if the total integrated fluorescence of the test sample is within two standard deviations of the expected photometric response of the photodetector.

13. A method for assaying the concentration of an analyte which forms an analyte complex with a binding agent in a competition reaction, comprising the steps of:

labeling the binding agent with a detectable first label;

labeling an antigen with a detectable second label, wherein the antigen is capable of forming an antigen complex with the specific binding agent;

contacting the analyte and the labeled antigen with an amount of the labeled binding agent to produce a reaction mixture including the labeled binding agent, the analyte complex, the labeled antigen, and the antigen complex;

providing a separation medium upon which the labeled binding agent and the antigen and analyte complexes migrate at different velocities;

separating the labeled binding agent and the antigen and analyte complexes by applying said reaction mixture to the separation medium for separation by electrophoresis;

measuring and recording the migration of the labeled binding agent, the analyte complex, and the antigen complex between at least two reference points on the separation medium by detecting the first label, wherein the recorded migration of the labeled binding agent, the analyte complex, and the antigen complex are characterized as peaks;

measuring and recording the migration of the labeled antigen and the antigen complex between at least two reference points on the separation medium by detecting the second label, wherein the recorded migration of the antigen and the antigen complex are characterized as peaks;

measuring the area under the peaks of the measured labeled binding agent, analyte complex, and antigen complex according to the detected first label;

measuring the area under the peaks of the measured labeled antigen, and antigen complex according to the detected second label;

determining a ratio between the area under the peak of the measured labeled antigen and the area under the peaks of the measured antigen and analyte complexes; and determining the concentration of analyte by relating the determined ratio to an assay standard curve representing the competition reaction between the analyte and antigen for the binding agent.

14. The method according to claim 13 further including the step of comparing the migration measured for the antigen complex using the first label with the migration measured for the antigen complex using the second label as a check on the quality of the assay.

15. The method according to claim 14 further including the step of stopping the assay if the migration measured for the antigen complex using the first label is different from the migration measured for the antigen complex using the second label.

* * * * *